United States Patent

Takada et al.

[11] Patent Number: 4,690,930
[45] Date of Patent: Sep. 1, 1987

[54] PYRAZOLO[4,3-C]QUINOLINE-3-ONE AND IMIDAZO[4,3-C]CINNOLIN-3-ONE DERIVATIVES AND THEIR USE AS PSYCHOTROPIC AGENTS

[75] Inventors: Susumu Takada, Hyogo; Takashi Sasatani, Nara; Hirohisa Shindo, Osaka; Akira Matsushita, Hyogo; Masami Eigyo, Nara, all of Japan

[73] Assignee: Shionogi & Co., Ltd, Osaka, Japan

[21] Appl. No.: 795,168

[22] Filed: Nov. 5, 1985

[30] Foreign Application Priority Data

Nov. 5, 1984 [JP] Japan .................. 59-233511

[51] Int. Cl.$^4$ .................. A61K 31/415; C07D 471/04; C07D 237/28
[52] U.S. Cl. .................... 514/293; 514/248; 546/82; 544/234
[58] Field of Search .................. 546/82; 544/234; 514/293, 248

[56] References Cited

U.S. PATENT DOCUMENTS 4,479,955 10/1984 Yokoyama .................. 544/234

FOREIGN PATENT DOCUMENTS 2131801A 6/1984 United Kingdom .................. 546/82

OTHER PUBLICATIONS

Fryer et al., Life Sciences, vol. 39, pp. 1947–1957, (1986).
Goodnick et al., J. Clin. Psychiatry 45; 5 May 1984.
File, S. E., Neuroscience Letters, 35, (1983), 317–320.
Peterson, E. N., European J. of Pharmacology 94, (1983), 117–124.
Ghoneim et al., Psychopharmacology, (1977).
Block et al., Experimental Aging Research, vol. II, No. 3, fall 1985.
Tamminga et al., The Lancet, Jul. 9, 1983, pp. 98–99.
Braestnip et al., Bioch. Pharm., vol. 33, No. 6, pp. 859–862, (1984).
Jensen et al., Psychopharmacology, 64, (1979).
Yenault et al., Nature, vol. 321, 26 Jun. 1986.
Katrizky et al, Comprehensive Heterocyclic Chemistry, vol. 4, p. 810, (1984), Pergamon Press.
B von M. Hentschel et al., J. prakt. Chem., 316, 878–880, (1974).
Huddleston et al, J. Chem. Research (S), 1980, 238–239.

Primary Examiner—John M. Ford
Assistant Examiner—J. Richter
Attorney, Agent, or Firm—Birch, Stewart, Kolasch & Birch

[57] ABSTRACT

Compounds of the formula (I):

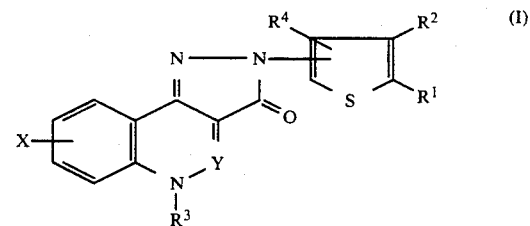

wherein $R^1$ and $R^2$ each is hydrogen, alkyl, alkoxycarbonyl, carboxy, halogen, nitro or trifluoromethyl, or $R^1$ and $R^2$ taken together may form alkylene; $R^3$ is hydrogen, alkyl, alkanoyl or alkylsulfonyl; $R^4$ is hydrogen, alkoxycarbonyl, carboxy or halogen; X is hydrogen, alkyl, alkoxy, halogen or hydroxy; and Y is methine or nitrogen or salts thereof are provided. The compounds (I) show potent psychotropic activity.

13 Claims, No Drawings

PYRAZOLO[4,3-C]QUINOLINE-3-ONE AND IMIDAZO[4,3-C]CINNOLIN-3-ONE DERIVATIVES AND THEIR USE AS PSYCHOTROPIC AGENTS

BACKGROUND OF THE INVENTION

1. Field of the Invention

The present invention relates to thienyl condensed pyrazole derivatives which show potent psychotropic activity.

2. Prior Art

2-Phenylpyrazolo[4,3-c]quinolin-3-one derivatives have an affinity to benzodiazepine receptor and are known as useful psychotropic agents such as antidepressant and tranquilizer [U.S. Pat. No. 4,312,870]. Furthermore, it is known that 2-thiazolylpyrazolo[4,3-c]quinolin-3-one derivatives have the same utility as said derivatives [U.S. Pat. No. 4,524,146], but thienyl-substituted compounds of the latter are not disclosed illustratively.

BRIEF SUMMARY OF THE INVENTION

The present invention relates to compounds of the formula (I):

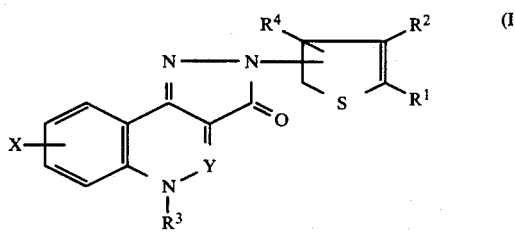

(wherein $R^1$ and $R^2$ each is hydrogen, alkyl, alkoxycarbonyl, carboxy, halogen, nitro or trifluoromethyl, or $R^1$ and $R^2$ taken together may form alkylene; $R^3$ is hydrogen, alkyl, alkanoyl or alkylsulfonyl; $R^4$ is hydrogen, alkoxycarbonyl, carboxy or halogen; X is hydrogen, alkyl, alkoxy, halogen or hydroxy; and Y is methine or nitrogen) or salts thereof.

DETAILED DESCRIPTION OF THE INVENTION

The present invention relates to the compounds of the formula (I):

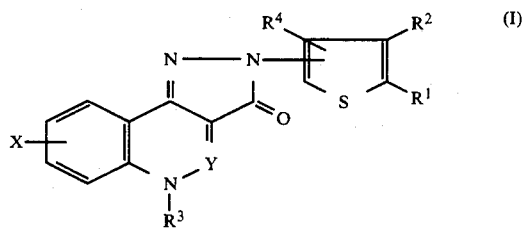

(wherein $R^1$ and $R^2$ each is hydrogen, alkyl, alkoxycarbonyl, carboxy, halogen, nitro or trifluoromethyl, or $R^1$ and $R^2$ taken together may form alkylene; $R^3$ is hydrogen, alkyl, alkanoyl or alkylsulfonyl; $R^4$ is hydrogen, alkoxycarbonyl, carboxy or halogen; X is hydrogen, alkyl, alkoxy, halogen or hydroxy; and Y is methine or nitrogen) or salts thereof.

The compounds (I) of the present invention are useful as psychotropic agents.

The compounds (I) can be prepared according to Methods A, B, and/or C.

Method A

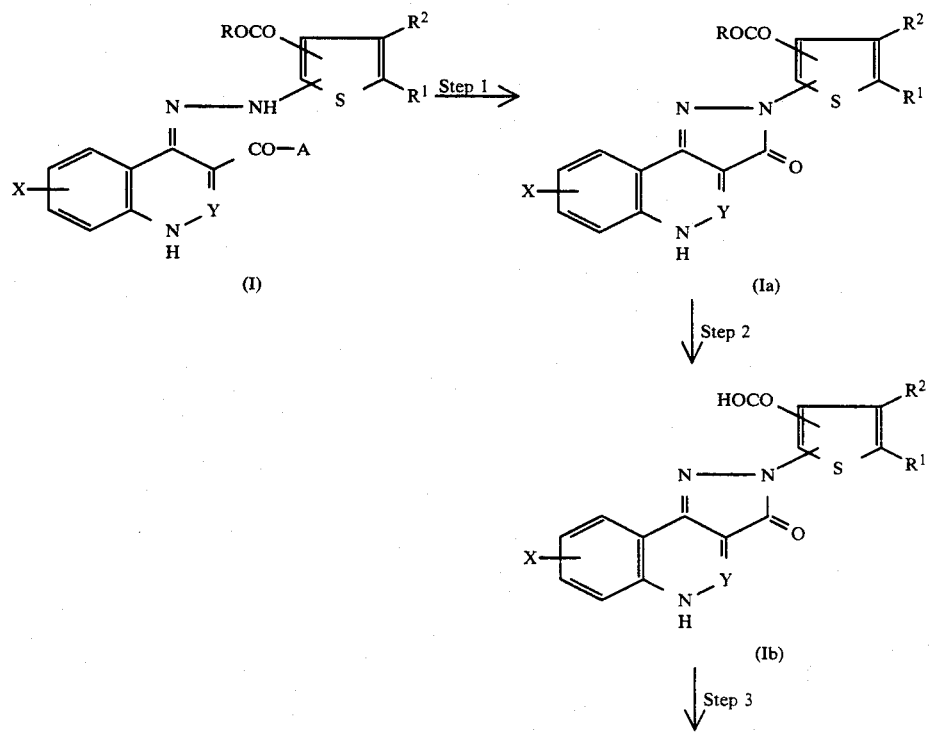

-continued
Method A

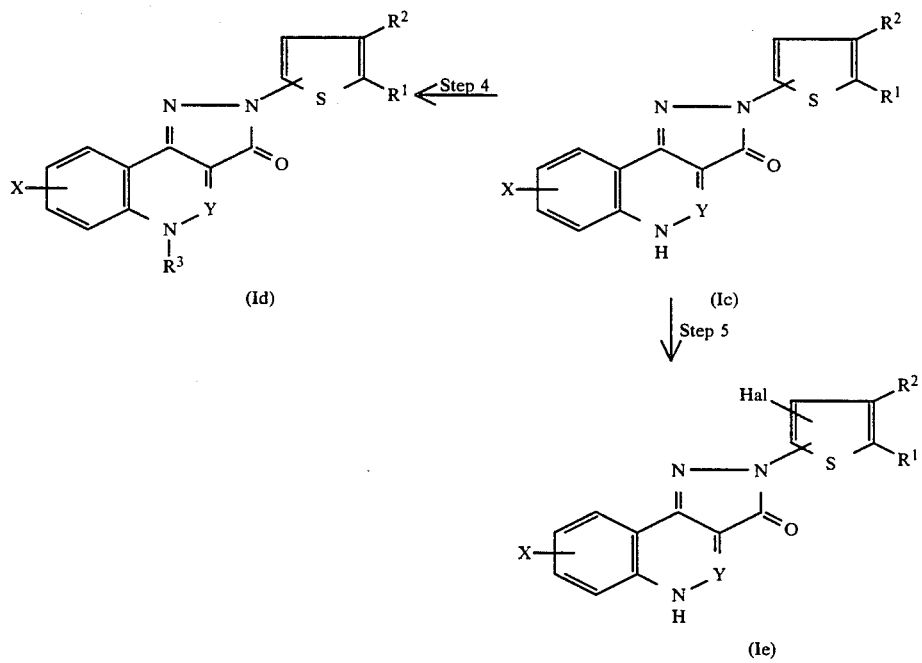

(wherein A is a leaving group; Hal is halogen; R is alkyl; and $R^1$, $R^2$, X, and Y each has the same meaning as defined above).

Steps 1 to 5 each will be explained below.

Step 1

The compound (Ia) is prepared by cyclization of the starting material (II) in this step. This reaction can be carried out in a solvent such as alkanols (e.g. methanol, ethanol, isopropanol, etc.), halogenohydrocarbons (e.g. dichloromethane, dichloroethane, chloroform, carbon tetrachloride, etc), aromatic solvents (e.g. benzene, toluene, xylene, etc.), or dimethylformamide; at a temperature of about 10°~about 100° C., if required in the presence of an inorganic base such as alkali hydroxide (e.g. potassium hydroxide, sodium hydroxide, lithium hydroxide, etc.), alkali carbonate (e.g. potassium carbonate, sodium carbonate, etc.), alkali bicarbonate (e.g potassium bicarbonate, sodium bicarbonate, etc.), and the like; an organic base such as triethylamine, pyridine, picoline, quinoline, piperidine, pyrrolidine, N-methylmorpholine, and the like; an inorganic acid such as hydrochloric acid, sulfuric acid, phosphoric acid, and the like; and an organic acid such as acetic acid, trifluoroacetic acid, toluenesulfonic acid, and the like.

The base or acid may be selected in accordance with the properties of the substituents on the thienyl group of the starting material (II) and the properties of the leaving group A. The reaction is preferably carried out at a temperature of about 10°~about 30° C., if a base or an acid is used.

The reaction may be accelerated under inert gas flow such as nitrogen, argon, etc.

The starting material (II) is, for example, provided according to the following method.

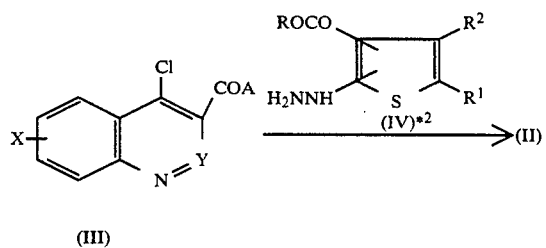

(wherein A, R, $R^1$, $R^2$, X, and Y each has the same meaning as defined above).
*1J. Am. Chem. Soc., 68, 1264 (1964); J. Org. Chem., 18, 55 (1953)
*2J. Prakt. Chem., 316, 878 (1974)

Step 2

The compound (Ia) is hydrolyzed to give the compound (Ib) in this step. The reaction can be conducted in a conventional manner of hydrolysis. For example, the reaction can be carried out by treating the compound (Ia) with an inorganic base in a solvent. As the solvent, water; alkanols (e.g. methanol, ethanol, isopropanol, etc.); halogenohydrocarbons (e.g. dichloromethane, dichloroethane, chloroform, carbon tetrachloride, etc.); ethers (e.g. ether, tetrahydrofuran, dioxane, etc.); dimethylformamide; dimethylsulfoxide, and the like or the mixture thereof may be used. As the inorganic base, alkali hydroxide, alkali carbonate, alkali bicarbonate, and the like may be employed. The reaction is performed at a temperature of about 30°~about 120° C., preferably, about 50°~about 80° C. under inert gas flow such as nitrogen or argon in the same manner as in Step 1. Step 2 can be carried out continuously after Step 1.

Step 3

The decarboxylation of the thiophene carboxylic acid (Ib) is perfomed in an organic solvent such as quinoline, isoquinoline, and the like. at a temperature of about 150°~about 250° C., if necessary, in the presence of a catalyst such as copper powder, chromous acid-copper (CuO.Cr$_2$O$_3$), etc.

The reaction can also be achieved as follows. Thus, the compound (Ib) is converted into its alkali metal salt by treating with alkali hydroxide, and then the alkali metal salt of Ib is heated at about 150°~about 250° C. in the presence of a base (e.g. calcium oxide-sodium hydroxide etc.)

Step 4

The objective compound (Id) is prepared by introduction of an alkanoyl to the compound (Ic) or alkylation of Ic. The reaction is conducted with an alkylating agent or alkanoyl indroducing agent in an appropriate solvent in the presence of an alkali hydride such as sodium hydride, potassium hydride, and the like. The reaction is carried out at a temperature of 30°~120° C. As the alkylating agent, alkyl halide (e.g. methyl bromide, ethyl iodide, propyl chloride, etc.), dialkyl sulfate (e.g. dimethyl sulfate, diethyl sulfate, etc.), and the like may be used. As the alkanoyl introducing agent, alkanoyl halide (e.g. acetyl chloride, butyryl bromide, etc.) or alkanoic acid anhydride (e.g. acetic anhydride, propionic anhydride) can be used. As the solvent, tetrahydrofuran, dioxane, diglyme, dimethylformamide, and the like are preferred.

Step 5

The compound (Ie) is prepared by halogenation of the compound (Ic). The halogenation can be performed by reacting the compound (Ic) with halogen such as fluorine, chlorine, bromine, iodine, etc. in an appropriate solvent in a conventional manner. As the solvent, halogenohydrocarbons such as dichlormethane, dichloroethane, chloroform, carbon tetrachloride, and the like may be employed. The reaction is accomplished at a temperature of room temperature to refluxing temperature within a period of several hours to several tens hours.

The halogenation can also be achieved by using N-bromosuccinimide, N-chlorosuccinimide, sulfuryl chloride, and the like.

The compound (Ic) may be also prepared according to the following Method B.

Method B

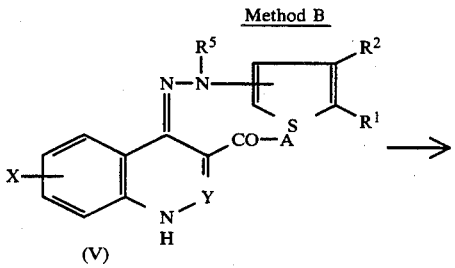

(wherein A, R$^1$, R$^2$, X, and Y each has the same meaning as defined above; R$^5$ is alkoxycarbonyl, acetyl, or trifluoroacetyl, etc.)

Method B is carried out by reacting the compound (V) with an acid at a temperature of room temperature to about 100° C. in an appropriate solvent, if required by addition of a base. As the acid, strong acid such as trifluoroacetic acid, hydrobromic acid-acetic acid may preferably be used. The base may be selected suitably from the group consisting of inorganic bases such as alkali hydroxide (e.g. potassium hydroxide, sodium hydroxide, lithium hydroxide, etc.); alkali carbonate (e.g. potassium carbonate, sodium carbonate, etc.); alkali bicarbonate (e.g. potassium bicarbonate, sodium bicarbonate, etc.); organic base such as triethylamine, pyridine, picoline, quinoline, piperidine, pyrrolidine, N-methylmorpholine, and the like. The solvent used in the reaction is exemplified by alkanols (e.g. methanol, ethanol, isopropanol, etc.); halogenohydrocarbons (e.g. dichloromethane, dichloroethane, chloroform, carbon tetrachloride, etc.); ethers (e.g. dibutyl ether, tetrahydrofuran, etc.), and the like.

The reaction is accomplished over a period of several tens minutes to several hours, by which the compound (Ic) is produced.

The compound (Id) and the compound (Ie) are prepared from the compound (Ic) in the same manner as in Steps 4 and 5 respectively in Method A.

The objective compound (I) wherein R$^1$ is hydrogen can be prepared by the following Method C.

Method C

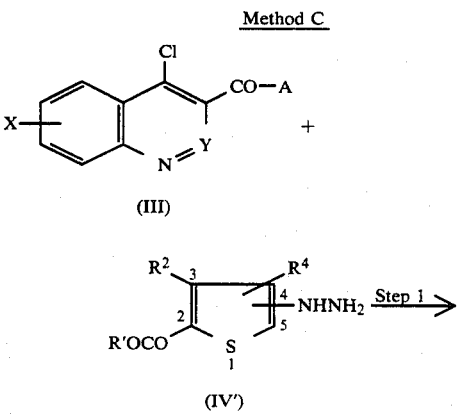

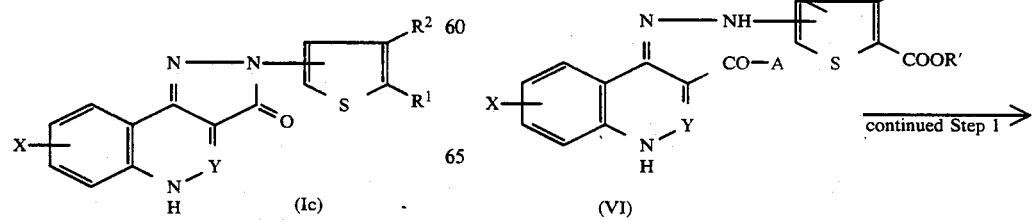

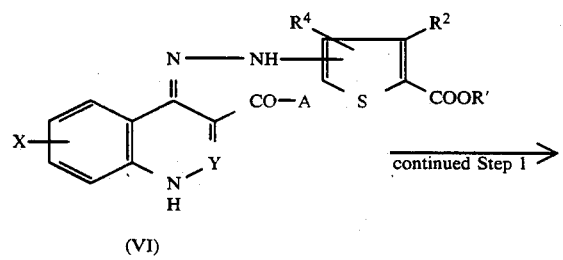

-continued
Method C

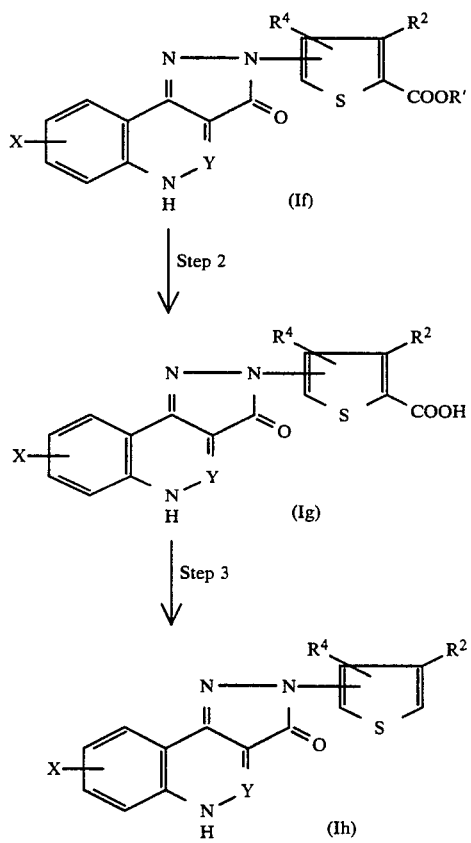

(wherein A, R², R⁴, X, and Y each has the same meaning as defined above; R' is alkyl).

Steps 1 to 3 can be conducted as follows.

Step 1

The compound (IV') in which the thiophene is protected at the 2 position is used in this step. For example, the compound (IV') protected by alkoxycaronyl (R'O—CO—) or an acid addition salt such as hydrochloride of the compound (IV') is allowed to react with the compound (III) in an appropriate solvent at a temperature of about 10°~about 100° C., if required by addition of a base or an acid. The solvent includes alkanols (e.g. methanol, ethanol, isopropanol, etc.); halogenohydrocarbons (e.g. dichlorometahne, dichloroethane, chloroform, carbon tetrachloride, etc.); aromatic solvents (e.g. benzene, toluene, xylene, etc.); dimethylformamide, and the like. As the base, inorganic bases such as alkali hydroxide, alkali carbonate, alkali bicarbonate, and the like; organic bases such as triethylamine, pyridine, picoline, quinoline, piperidine, pyrrolidine, N-methylmorpholine, and the like may be used. As the acid, inorganic acids such as hydrochloric acid, sulfuric acid, phosphoric acid, and the like, and organic acids such as acetic acid, trifluoroacetic acid, toluenesulfonic acid, and the like can be employed.

In this step it seemed that the compound (IV) would be produced as an intermediate, while the cyclized compound (If) has been directly provided.

Step 2

The compound (Ig) is prepared by hydrolysis of the compound (If) in this step.

In this step, the reaction may be conducted in the same manner as in Step 2 of Method A. This reaction may be conducted in a conventional manner for hydrolysis, for example, it is carried out by treating with an inorganic base in an appropriate solvent.

The solvent includes water; alkanols (e.g. methanol, ethanol, isopropanol, etc.); halogenohydrocarbons (e.g. dichloromethane, dichloroethane, chloroform, carbon tetrachloride, etc.); ethers (e.g. ether, tetrahydrofuran, dioxane, etc.); dimethylformamide; dimethylsulfoxide, and a mixture thereof. As the inorganic base, alkali hydroxide, alkali carbonate, alkali bicarbonate, and the like may be employed. The reaction may be carried out at a temperature of about 30° to about 120° C., preferably, about 50° to about 80° C., under inert gas flow such as nitrogen, argon, and so on.

Step 3

The compound (Ih) can be prepared by decarboxylation of the compound (Ig) in this step; the reaction may be carried out in the same manner as in Step 3 of Method A.

The reaction can be carried out in a solvent such as quinoline, isoquinoline, etc. at a temperature of about 150° to about 250° C., if necessary, in the presence of a catalyst such as copper powder, chromous acid-copper (CuO.Cr₂O₃), etc.

The reaction can also be achieved as follows. Thus, the compound (Ig) is converted into its alkali metal salt by treating with alkali hydroxide, and then the alkali metal salt of Ig is heated at about 150° to about 250° C. in the presence of a base (e.g. calcium oxide-sodium hydroxide etc.)

In Method C, Steps 1 to 3 can be carried out continuously, or the product in each step can be isolated.

The compound (Ih) can be subjected to alkylation or introduction of alkanoyl in the same manner as in Step 4 of Method A. The compound (Ih) can be halogenized in the same manner as in Step 5 in Method A.

The objective compound (I) can also be prepared by cyclizing a 4-[2(3)-thienylhydrazono]-3-carboxylic acid ester. The ester is provided from the compound in which the substituent on the thiophene of the corresponding compound (IV) or (IV') (i.e. alkoxycarbonyl ROCO—, R'OCO—) is replaced by an electron-withdrawing group such as nitro.

The terms used in the above definitions are illustratively explained below.

The alkyl includes $C_1$–$C_5$ alkyl such as methyl, ethyl, n-propyl, isopropyl, n-butyl, tert-butyl, n-pentyl, isopentyl, and the like.

The alkoxy includes $C_1$–$C_5$ alkoxy, for example, methoxy, ethoxy, n-propoxy, isopropoxy, butoxy, pentyloxy, and the like.

The alkanoyl is exemplified by $C_1$–$C_5$ alkanoyl, such as formyl, acetyl, propionyl, butryl, valeryl, and the like.

The alkoxycarbonyl includes $C_2$–$C_5$ alkoxycarbonyl such as methoxycarbonyl, ethoxycarbonyl, n-propoxycarbonyl, isopropoxycarbonyl, n-butoxycarbonyl, sec-butoxycarbonyl, tert-butoxycarbonyl, and the like.

The alkylene is exemplified by $C_3$–$C_4$ alkylene such as trimethylene and tetramethylene.

The alkylsulfonyl includes $C_1$-$C_5$ alkylsulfonyl such as methylsulfonyl, ethylsulfonyl, n-propylsulfonyl, isopropylsulfonyl, n-butylsulfonyl, tert-butylsulfonyl, n-pentylsulfonyl, isopentylsulfonyl, and the like.

The halogen includes fluorine, chlorine, bromine, iodine, and the like.

As the representatives of the leaving group are alkoxy such as methoxy, ethoxy, n-propoxy, isopropoxy, n-butoxy, isobutoxy, sec-butoxy, and tert-butoxy. The objective compounds (I) can be converted into inoganic aor organic acid addition salt thereof, if required. The inorganic acid includes hydrochloric acid, hydrobromic acid, sulfuric acid, phosphoric acid, nitric acid, and the like; the organic acid includes acetic acid, methanesulfonic acid, succinic acid, maleic acid, tartaric acid, benzoic acid, and the like.

The compounds (I) can be converted into alkali metal salt thereof such as sodium, potassium, or lithium salt thereof.

The objective compound (I) wherein $R^3$ is hydrogen can be exist as a tautomer.

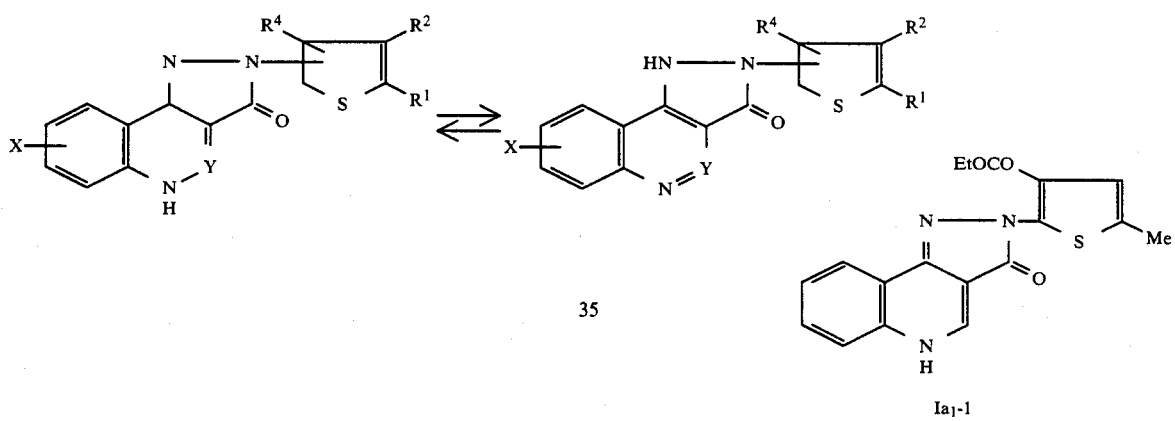

(wherein $R^1$, $R^2$, $R^4$, X, and Y each has the same meaning as defined above).

The objective compounds (I) or salts thereof have a high affinity to a benzodiazepine-receptor, and they are useful as psychotropic agents such as minor tranquilizers, anticonvulsants, agents for treating benzodiazepine intoxication, or activators of mentation.

The compound of the present invention can be administered orally or parenterally to human beings or other mammals.

The compound of the present invention can be formulated as tablets, capsules, pills, granules, injections, suppositories, and syrups in a conventional manner. As pharmaceutically acceptable diluents, lactose, sucrose, wheat starch, potato starch, magnesium stearate, gelatin, methyl cellose, agar, water and the like can be used. If required, stabilizers, emulsifiers, buffers, and other additives can be added.

The compounds (I) can be administered orally at a dose or doses of 0.1~500 mg per day.

The present invention will be explained in more detail by the following Examples, Referential Examples, and Preparations.

The abbreviations used in Examples, Referetial Examples, and Tables each has the following meanings.

Me: methyl; Et: ethyl; Bu:butyl; (d): decomposition point

EXAMPLE 1

(1)
2-[2-(3-Ethoxycarbonyl-5-methylthienyl)]-2,5-dihydro-3H-pyrazolo[4,3-c]quinolin-3-one $Ia_1$-1

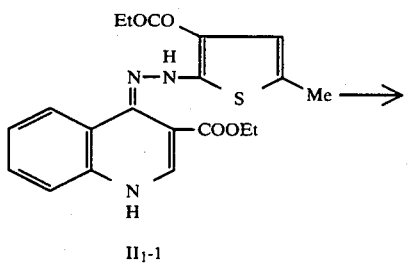

$II_1$-1

To a suspension of 1.04 g of ethyl 4-[2-(3-ethoxycarbonyl-5-methylthienyl)hydorazono]-1,4-dihydroquinoline-3-carboxylate $II_1$-1 in 15 ml of ethanol is added 4 ml of 1N sodium hydroxide under nitrogen gas at room temperature. The mixture is stirred for 30 minutes, acidified with acetic acid, and dried up under reduced pressure. The residue is mixed with water, filtered, and washed with water and ethanol. The resulting solid is crystallized from chloroform-ethyl acetate to give 1.17 g of yellowish crystalline $Ia_1$-1. This is recrystallized from chloroform-ethyl acetate to give yellowish crystals, melting at 248°~250° C. (d).

(2)
2-[2-(3-Carboxy-5-methylthienyl)]-2,5-dihydro-3H-pyrazolo[4.3-c]quinolin-3-one $Ib_1$1

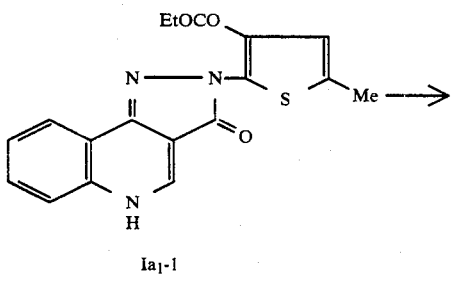

$Ia_1$-1

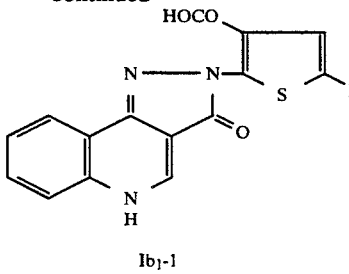

(Ib₁-1)

To a suspension of 707 mg of 2-[2-(3-ethoxycarbonyl-5-methylthienyl)]-2,5-dihydro-3H-pyrazolo[4,3-c]quinolin-3-one Ia₁-1 in 10 ml of methanol is added 10 ml of 1N sodium hydroxide. The mixture is stirred at 60° C. for 1 hour, cooled, neutralized with 10 ml of 1N hydrochloric acid, and acidified with acetic acid. The precipitating crystalline material is collected by filtration, washed with ater, and dried to give 637 mg of yellowish crystalline Ib₁-1. m.p.: 300°–303° C. (d).

Ib₁-1 can be directly provided from IIb₁-1 in the same treatment as in the above description.

EXAMPLES 2–13

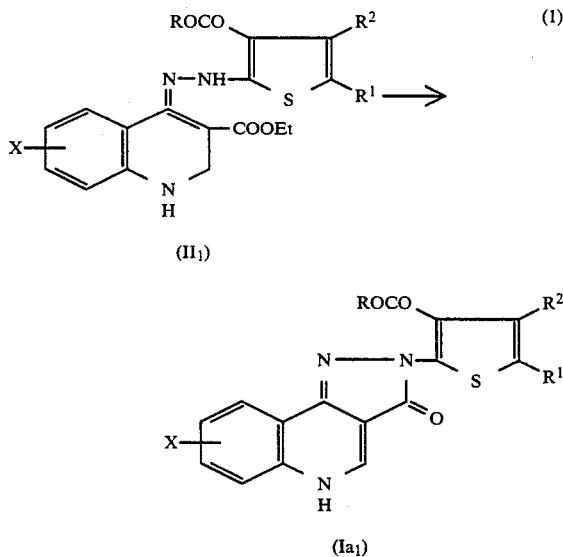

To a suspension of an ethyl 4-[2-(3-alkoxycarbonyl-thienyl)-hydrazono]-1,4-dihydroquinoline-3-carboxylate (II₁) in ethanol is added aqueous 1N sodium hydroxide under nitrogen gas at room temperature. The mixture is stirred for about several 10 minutes to about several hours, acidified with acetic acid, and dried up under reduced pressure. The residue is washed with water and ethanol in order. The reslting solid is crystallized from chloroform-ethyl acetate to give yellow crystalline Compound (Ia₁).

(2)

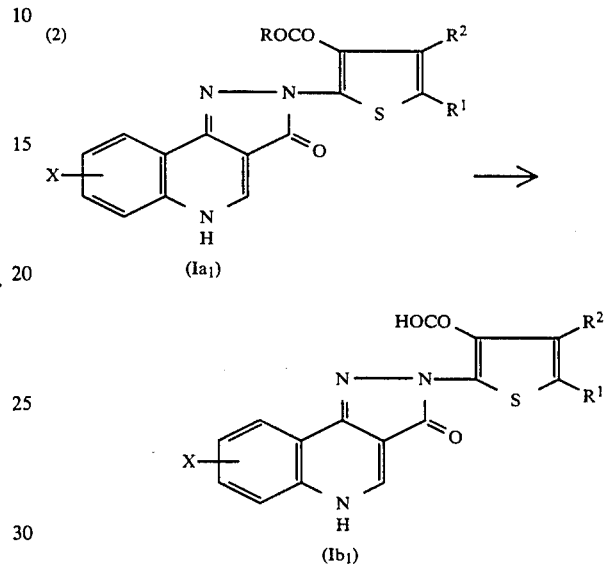

To a suspension of a 2-[2-(3-alkoxycarbonylthienyl)]-2,5-dihydro-3H-pyrazolo[4,3-c]quinolin-3-one (Ia₁) in methanol is added aqueous 1N sodium hydroxide under nitrogen gas. The mixture is stirred under heating for about several 10 minutes to about several hours. After cooling, the mixture is neutralized with 1N hydrochloric acid and acidified with acetic acid. The precipitating crystals are collected by filtration, washed with water, and dried to give a 2-[2-(3-carboxythienyl)]-2,5-dihydro-3H-pyrazolo[4,3-c]quinolin-3-one (Ib₁).

The reaction conditions to prepare Compound (Ia₁) from corresponding Compound (II₁), yield (g), (%), structural formulae, recrystallization solvent, and melting point relative to the compound (Ia₁) are summarized in Table 1.

The reaction conditions to prepare Compound (Ib₁) from corresponding Compound (Ia₁), yield (g), (%), structural formulae, appearance, and decomposition point of the compound (Ib₁) are shown in Table 2.

TABLE 1

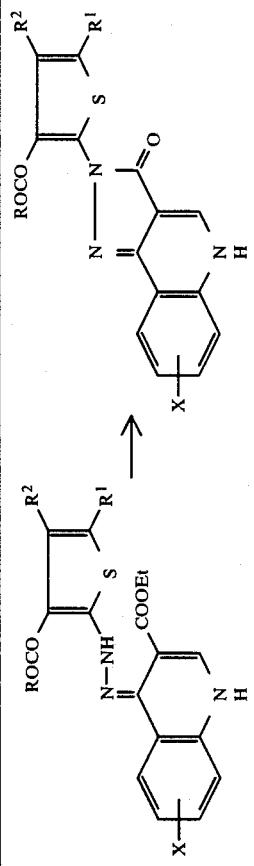

| Ex. No. | Amount of Compound $(II_1)$ (g) | ethanol (ml) | 1N NaOH (ml) | reaction time (hrs) | yield (g) | yield (%) | Compd. No. | $R^1$ | $R^2$ | R | X | crystal water | recrystallization solvent | m.p. (°C.) |
|---|---|---|---|---|---|---|---|---|---|---|---|---|---|---|
| 2 | 0.82 | 10 | 2.2 | 0.5 | 0.66 | 90 | Ia₁-2 | Et | H | Et | H | ¼ H₂O | CHCl₃—EtOAc | 175-178 |
| 3 | 0.92 | 8 | 2.5 | 1 | 0.52 | 66 | Ia₁-3 | Me | Me | Et | H | — | CHCl₃—MeOH | 252-253 |
| 4 | 0.63 | 7 | 1.6 | 0.8 | 0.475 | 88 | Ia₁-4 | —(CH₂)₄— | | Et | H | — | CHCl₃MeOH | 281-284 |
| 5 | 2.14 | 70 | 10 | 1 | 1.80 | 93 | Ia₁-5 | n-Bu | H | Et | H | — | n-hexane-EtOH | 210-212 |
| 6 | 1.04 | 20 | 2.9 | 1 | 0.88 | 96 | Ia₁-6 | Me | H | Me | 8-Me | H₂O | MeOH | 162-164d |
| 7 | 1.15 | 50 | 3.4 | 1 | 0.93 | 91 | Ia₁-7 | Me | H | Me | 8-MeO | — | MeOH | 255-259 |
| 8 | 0.98 | 20 | 2.6 | 1.5 | 0.80 | 92 | Ia₁-8 | Me | H | Me | 8-Cl | H₂O | MeOH | 166-169 |
| 9 | 1.05 | 20 | 2.9 | 1 | 0.865 | 93 | Ia₁-9 | Me | H | Me | 8-F | 1/5 H₂O | MeOH—benzene | 168-171 |
| 10 | 0.70 | 5 | 1.9 | 1 | 0.55 | 88 | Ia₁-10 | Me | H | Me | 7-Me | — | EtOH | 246-248 |
| 11 | 1.67 | 100 | 8.0 | 1 | 1.36 | 93 | Ia₁-11 | Me | H | Me | 7-Cl | — | EtOH | 261-263 |
| 12 | 0.472 | 5 | 1.2 | 0.7 | 0.386 | 90 | Ia₁-12 | COOEt | Me | Et | H | — | CHCl₃—EtOH | 282-285 |
| 13 | 2.36 | 50 | 6.6 | 0.5 | 1.99 | 94 | Ia₁-13 | H | COOEt | Et | H | ½ H₂O | MeOH | 255-258 |

TABLE 2

(Ia₁) → (Ib₁)

| Ex. No. | Amount of Compound (Ia₁) (g) | methanol (ml) | 1N NaOH (ml) | reaction temperature (°C.) | reaction time (hrs) | yield (g) | yield (%) | Compd No. | R¹ | R² | X | crystal water | appearance | dec. point (°C.) |
|---|---|---|---|---|---|---|---|---|---|---|---|---|---|---|
| 2 | 0.558 | 10 | 10 | 40 | 1.5 | 0.481 | 92 | Ib₁-2 | Et | H | H | ½ H₂O | yellow | 280–283 |
| 3 | 0.500 | 5 | 10 | reflux | 2 | 0.35 | 76 | Ib₁-3 | Me | Me | H | ½ H₂O | yellow | 289–291 |
| 4 | 0.48 | 5 | 8 | reflux | 2 | 0.429 | 96 | Ib₁-4 | —(CH₂)₄— | | H | ½ H₂O | yellow | 294–296 |
| 5 | 0.70 | 10 | 5.4 | reflux | 0.5 | 0.630 | 95 | Ib₁-5 | n-Bu | H | H | ½ H₂O | yellow | 280–281 |
| 6 | 0.82 | 8 | 10 | 60 | 0.5 | 0.716 | 91 | Ib₁-6 | Me | H | 8-Me | 1/5 H₂O | yellow | 293–294.5 |
| 7 | 0.88 | 13 | 7.2 | reflux | 0.5 | 0.710 | 84 | Ib₁-7 | Me | H | 8-MeO | 2/5 H₂O | yellow | 295–2963 |
| 8 | 0.73 | 7 | 10 | 60 | 0.5 | 0.672 | 96 | Ib₁-8 | Me | H | 8-Cl | H₂O | yellow | 12–314 |
| 9 | 0.79 | 8 | 10 | 60 | 0.6 | 0.683 | 86 | Ib₁-9 | Me | H | 8-F | 3/5 H₂O | yellow | 299–301 |
| 10 | 0.436 | 8 | 4 | reflux | 0.5 | 0.375 | 86 | Ib₁-10 | Me | H | 7-Me | ½ H₂O | yellowish-green | 308–311 |
| 11 | 1.19 | 18 | 9.6 | reflux | 0.5 | 1.10 | 95 | Ib₁-11 | Me | H | 7-Cl | ½ H₂O | yellowish-green | 316–317 |
| 12 | 0.638 | 15 | 15 | 70 | 1.5 | 0.541 | 98 | Ib₁-12 | COOH | Me | H | 3/5 H₂O | yellowish-green | 248–251 |
| 13 | 0.350 | 5 | 5 | 60 | 1.5 | 0.229 | 75 | Ib₁-13 | Cl | COOH | H | ½ H₂O | yellow | >310 |

*Ib₁-13 is prepared from Ia₁-13' which is produced in Example 58.

EXAMPLE 14

2-[2-(5-Methylthienyl)]-2,5-dihydro-3H-pyrazolo[4,3-c]quinolin-3-one Ic₁-1

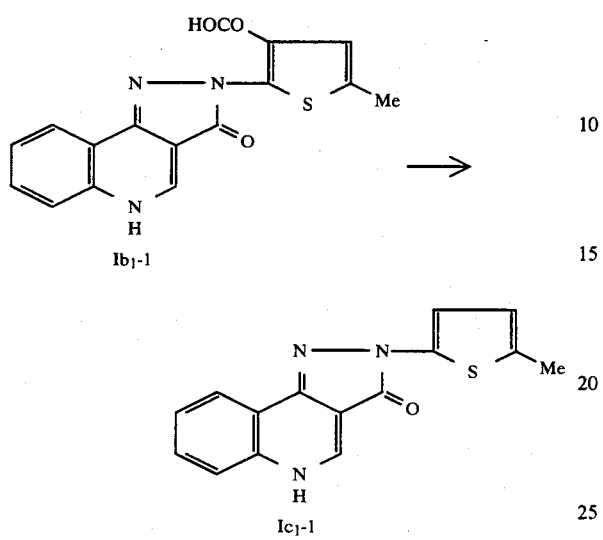

To a suspension of 390 mg of 2-[2-(3-carboxy-5-methylthienyl)]-2,5-dihydro-3H-pyrazolo[4,3-c]quinolin-3-one Ib₁-1 in 6 ml of quinoline is added 150 mg of copper powder. The mixture is stirred under nitrogen gas at 200° C. for 45 minutes. After cooling, copper powder is removed by filtration, and the filtrate is mixed with 1N sodium hydroxide and shaken with ether. The separated aqueous layer is filtered; and the filtrate is mixed with acetic acid. The precipitating crystals are collected by filtration and recrystallized from ethanol to give 280 mg of Ic₁-1 as yellow crystals.
m.p.: 309°–311° C. (d).

EXAMPLES 15–26

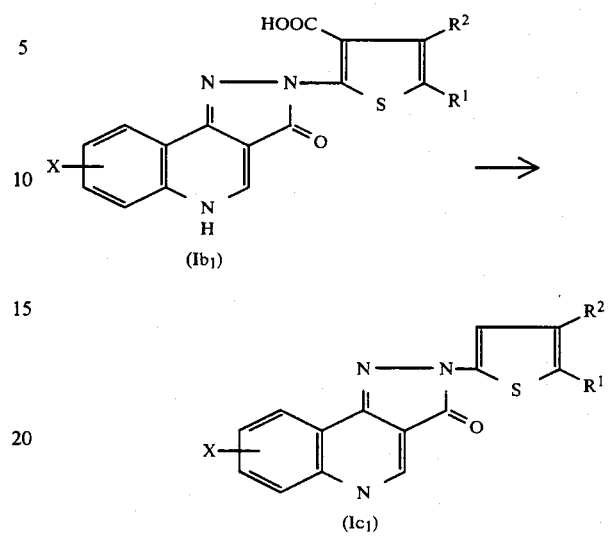

To a suspension of the compound (Ib₁) in quinoline is added copper powder. The mixture is stirred at a temperature of heating under nitrogen gas for several 10 minutes to several hours. After cooling, copper powder is removed by filtration, and the filtrate is mixed with 1N sodium hydroxide and shaken with ether. The separated aqueous layer is filtered; and the filtrate mixed with acetic acid. The precipitating crystalline material is collected by filtration and crystallized from an appropriate solvent to give the compound (Ic₁). The reaction conditiions to prepare the compound (Ic₁) from the compound (Ib₁); yield (g), (%), structural formulae, recrystallization solvent, and decomposition point of the compound (Ic₁) are shown in Table 3.

TABLE 3

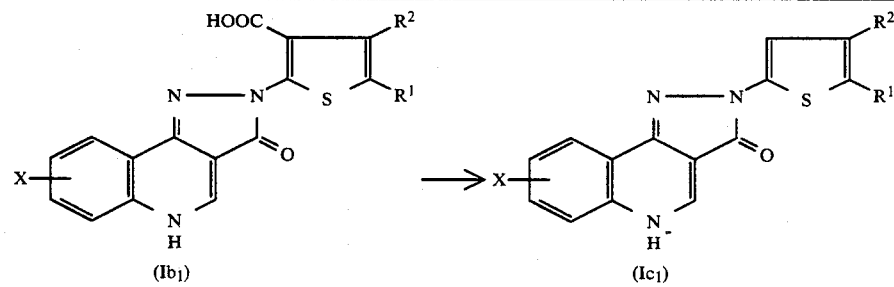

| Ex. No. | Amount of Compound (Ib₁) (g) | quinoline (ml) | copper powder (g) | reaction temperature (°C.) | reaction time (min) | yield (mg) | yield (%) | Compd. No. | R¹ | R² | X | crystal water | recrystallization solvent | dec. point (°C.) |
|---|---|---|---|---|---|---|---|---|---|---|---|---|---|---|
| 15 | 0.348 | 6 | 0.15 | 195 | 90 | 273 | 91 | Ic₁-2 | Et | H | H | ½ H₂O | EtOH | 277–280 |
| 16 | 0.339 | 5 | 0.12 | 195 | 20 | 182 | 63 | Ic₁-3 | Me | Me | H | H₂O | EtOH | 323–328 |
| 17 | 0.42 | 8 | 0.14 | 200 | 40 | 190 | 52 | Ic₁-4 | —(CH₂)₄— | | H | ½ H₂O | EtOH | 343–346 |
| 18 | 0.335 | 4 | 0.15 | 195 | 35 | 206 | 70 | Ic₁-5 | n-Bu | H | H | — | EtOH | 266–270 |
| 19 | 0.66 | 10 | 0.20 | 200 | 40 | 552 | 96 | Ic₁-6 | Me | H | 8-Me | — | CHCl₃—MeOH | 330–333 |
| 20 | 0.635 | 7 | 0.22 | 195 | 60 | 340 | 62 | Ic₁-7 | Me | H | 8-MeO | — | EtOH | 301–302 |
| 21 | 0.62 | 10.5 | 0.18 | 200 | 50 | 467 | 86 | Ic₁-8 | Me | H | 8-Cl | — | EtOH | 328–333 |
| 22 | 0.64 | 9.6 | 0.19 | 200 | 50 | 480 | 86 | Ic₁-9 | Me | H | 8-F | — | CHCl₃—MeOH | 320–325 |
| 23 | 0.70 | 7 | 0.24 | 195 | 60 | 372 | 63 | Ic₁-10 | Me | H | 7-Me | — | EtOH | 322–325 |
| 24 | 0.60 | 6 | 0.20 | 195 | 60 | 331 | 63 | Ic₁-11 | Me | H | 7-Cl | — | EtOH | 320–325 |
| 25 | 0.517 | 6 | 0.20 | 195 | 25 | 319 | 81 | Ic₁-12 | H | Me | H | — | EtOH | 310–312 |
| 26 | 0.200 | 4 | 0.20 | 200 | 20 | 114 | 80 | Ic₁-13 | Cl | H | H | H₂O | CHCl₃—MeOH | 309–312 |

EXAMPLE 27

(1)
2-[3-(2-Methoxycarbonylthienyl)]-2,5-dihydro-3H-pyrazolo[4,3-c]quinolin-3-one Ia₂-1

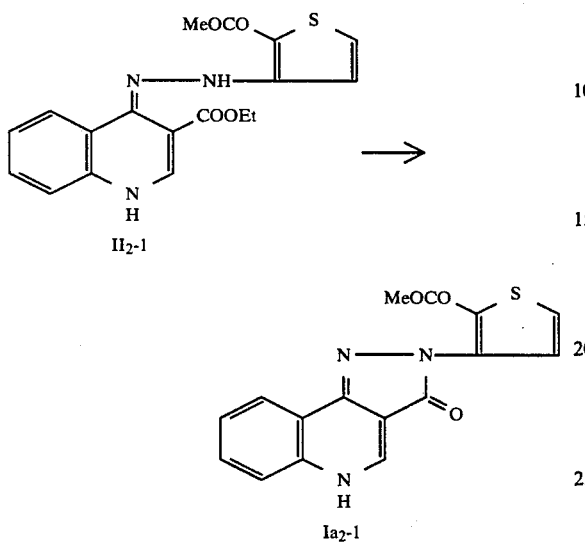

To a suspension of 1.04 g of ethyl 4-[3-(2-methoxycarbonylthienyl)hydrazono]-1,4-dihydroquinoline-3-carboxylate in 14 ml of ethanol (1.04 g) is added 3.4 ml of 1N sodium hydroxide under nitrogen gas at room temperture. The mixture is stirred for 10 minutes, acidified with acetic acid, and dried up under reduced pressure. The residue is mixed with water, filtered, washed with water, and recrystallized from ethanol to give 0.93 g (yield: 96%) of Ia₂-1 as yellow crystals.
m.p.: 240°–241° C.

(2)
2-[3-(2-Carboxythienyl)]-2,5-dihydro-3H-pyrazolo[4,3-c]quinolin-3-one Ib₂-1

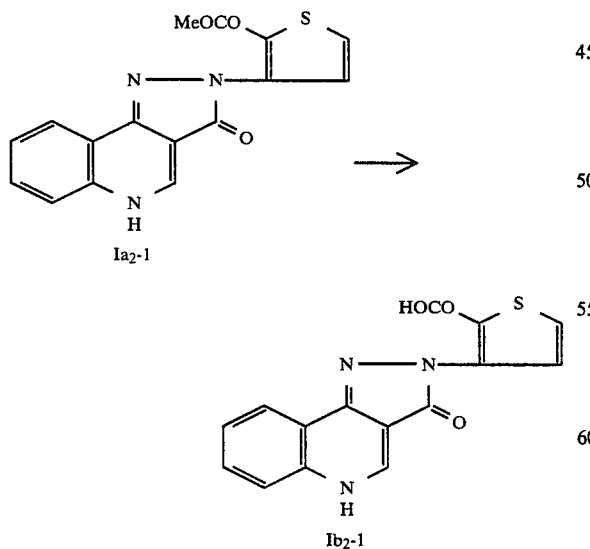

To a suspension of 515 mg of 2-[3-(2-methoxycarbonylthienyl)]-2,5-dihydro-3H-pyrazolo[4,3-c]quinolin-3-one Ia₂-1 in 7.5 ml of methanol is added 7.5 ml of 1N sodium hydroxide. The mixture is stirred at 40° C. for 1 hour and cooled. The resulting mixture is mixed with acetic acid; and the precipitating crystals are collected by filtration, washed with water, and dried to give 452 mg of Ib₂-1 as yellowish green crystals.
m.p.: 263–265 (d).

The compound Ib₂-1 can directly be prepared by reacting the compound II₂-1 in the above manner.

EXAMPLES 28–37

(1)

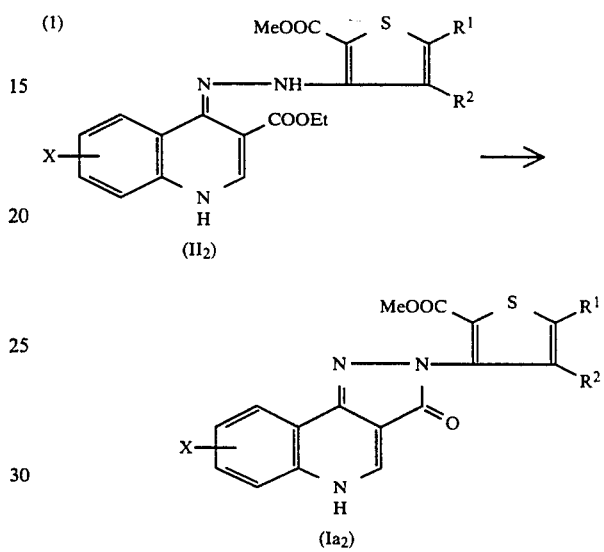

To a suspension of an ethyl 4-[3-(2-methoxycarbonylthienyl)-hydrazono]-1,4-dihydroquinoline-3-carboxylate (II₂) in ethanol is added 1N sodium hydroxide under nitrogen gas at room temperature. The mixture is stirred for about several 10 minutes to about several hours, acidified with acetic acid, and dried up under reduced pressure. The residue is mixed with water, filtered, washed with water, and recrystallized from an appropriate solvent to give yellow crystalline compound (Ia₂).

(2)

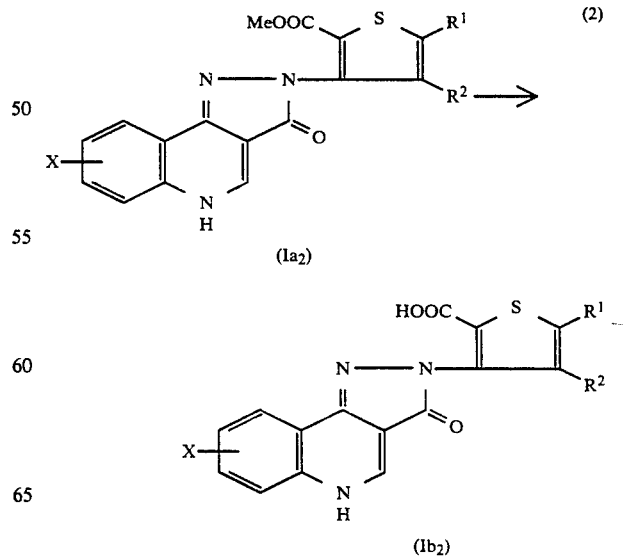

To a suspension of a 2-[3-(2-methoxycarbonyl-thienyl)]-2,5-dihydro-3H-pyrazolo[4,3-c]quinolin-3-one (Ia$_2$) in methanol is added 1N sodium hydroxide under nitrogen gas. The mixture is stirred for a period of about several 10 minutes to several hours with heating. After cooling, the reaction mixture is mixed with acetic acid; and the precipitating crystals are collected by filtration, washed with water, and dried to give a 2-[3-(2-carboxy-thienyl)]-2,5-dihydro-3H-pyrazolo[4,3-c]quinolin-3-one (Ib$_2$) as yellow crystals.

The reaction conditions to prepare the compound (Ia$_2$) from the corresponding compound (II$_2$), yield (g), (%), structural formulae, recrystallization solvent, and melting point of the compound (Ia$_2$) are shown in Table 4; the reaction conditions to prepare the compound (Ib$_2$) from the corresponding compound (Ia$_2$), yield, structural formulae, and decomposition point of the compound (Ib$_2$) are shown in Table 5.

TABLE 4

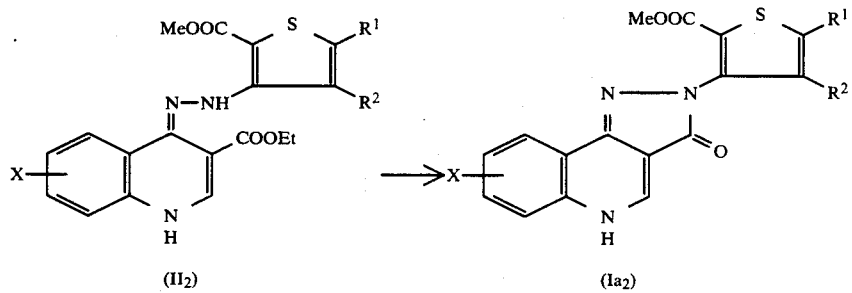

| Ex No. | Amount of Compound (II$_2$) (g) | ethanol (ml) | 1NNaOH (ml) | reaction time (min) | yield (g) | yield (%) | Compd. No. | R$^1$ | R$^2$ | X | crystal water | recrystallization solvent | m.p. (°C.) |
|---|---|---|---|---|---|---|---|---|---|---|---|---|---|
| 28 | 13.4 | 200 | 38 | 60 | 11.50 | 97 | Ia$_2$-2 | Me | H | H | H$_2$O | EtOH | 260–261 |
| 29 | 0.74 | 8 | 2.2 | 50 | 0.573 | 88 | Ia$_2$-3 | H | Me | H | — | EtOH | 265–167d |
| 30 | 0.95 | 19 | 2.6 | 80 | 0.66 | 79 | Ia$_2$-4 | Me | H | 8-Me | — | MeOH | 179–181d |
| 31 | 1.20 | 70 | 3.8 | 60 | 1.04 | 98 | Ia$_2$-5 | Me | H | 8-MeO | — | MeOH | 275–277 |
| 32 | 0.37 | 15 | 1.0 | 90 | 0.285 | 87 | Ia$_2$-6 | Me | H | 8-Cl | ½ H$_2$O | EtOH | 195–199 |
| 33 | 1.02 | 25 | 2.9 | 90 | 0.865 | 96 | Ia$_2$-7 | Me | H | 8-F | H$_2$O | MeOH | 189–191d |
| 34 | 0.945 | 50 | 4.7 | 120 | 0.575 | 69 | Ia$_2$-8 | Me | H | 7-Me | ¾ H$_2$O | MeOH | 153–156 |
| 35 | 1.45 | 69 | 6.9 | 90 | 1.04 | 81 | Ia$_2$-9 | Me | H | 7-Cl | — | EtOH | 167–169 |
| 36 | 0.66 | 5 | 1.8 | 60 | 0.55 | 94 | Ia$_2$-10 | Et | H | H | — | EtOH | 150–155 |
| 37 | 3.118 | 50 | 8.3 | 120 | 2.28 | 82 | Ia$_2$-11 | Me | H | 7-MeO | — | EtOH | 223–230 |

TABLE 5

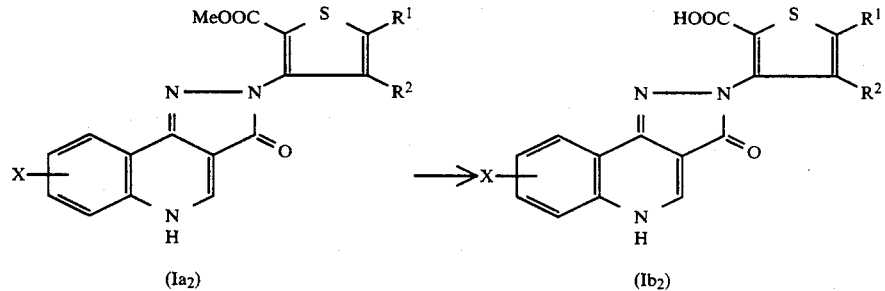

| Ex No. | Amount of Compound (Ia$_2$) (g) | methanol (ml) | 1NNaOH (ml) | reaction temperature (°C.) | reaction time (min) | yield (g) | yield (%) | Compd. No. | R$^1$ | R$^2$ | X | crystal water | dec. point (°C.) |
|---|---|---|---|---|---|---|---|---|---|---|---|---|---|
| 28 | 10.90 | 200 | 96 | reflux | 60 | 9.70 | 93 | Ib$_2$-2 | Me | H | H | ⅓ H$_2$O | 260–261 |
| 29 | 0.53 | 5 | 10 | 60 | 60 | 0.465 | 91 | Ib$_2$-3 | H | Me | H | ½ H$_2$O | 297–299 |
| 30 | 0.62 | 6 | 10 | 60 | 50 | 0.495 | 83 | Ib$_2$-4 | Me | H | 8-Me | 2/5 H$_2$O | 321–324 |
| 31 | 0.955 | 15 | 7.8 | reflux | 40 | 0.82 | 90 | Ib$_2$-5 | Me | H | 8-MeO | — | 307–312 |
| 32 | 0.67 | 6 | 10 | 60 | 40 | 0.592 | 92 | Ib$_2$-6 | Me | H | 8-Cl | 5/4 H$_2$O | 344–347 |
| 33 | 0.15 | 1.5 | 2 | 50 | 30 | 0.125 | 87 | Ib$_2$-7 | Me | H | 8-F | H$_2$O | 324–328 |
| 34 | 0.513 | 8 | 5 | reflux | 30 | 0.41 | 85 | Ib$_2$-8 | Me | H | 7-Me | ½ H$_2$O | 301–304 |
| 35 | 0.917 | 15 | 7.4 | reflux | 30 | 0.833 | 94 | Ib$_2$-9 | Me | H | 7-Cl | — | 337–340 |
| 36 | 0.44 | 8 | 3.7 | reflux | 60 | 0.42 | 98 | Ib$_2$-10 | Et | H | H | H$_2$O | >300 |
| 37 | 4.076 | 66 | 33 | reflux | 80 | 3.72 | 95 | Ib$_2$-11 | Me | H | 7-MeO | ½ H$_2$O | >300 |

EXAMPLE 38

2-(3-Thienyl)-2,5-dihydro-3H-pyrazolo[4,3-c]quinolin-3-one Ic$_2$-1

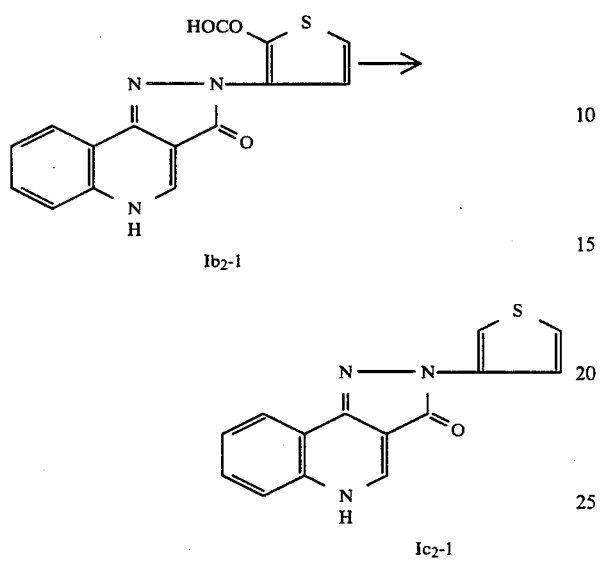

Ib$_2$-1

Ic$_2$-1

To a suspension of 400 mg of 2-[3-(2-carboxy-thienyl)]-2,5-dihydro-3H-pyrazolo[4,3-c]quinolin-3-one Ib$_2$-1 in 4 ml of quinoline is added 200 mg of copper powder. The mixture is stirred under nitrogen gas at 195° C. for 10 minutes; and copper powder is removed by filtration. The filtrate is mixed with 1N sodium hydroxide, extracted with ether to remove quinoline. The separated aqueous layer is filtered and the filtrate is mixed with acetic acid. The precipitating crystals are collected by filtration, washed with water, and recrystallized from ethanol to give 321 mg of Ic$_2$-1 as yellow crystals.

m.p.: 323°–325° C. (d).

EXAMPLES 39–48

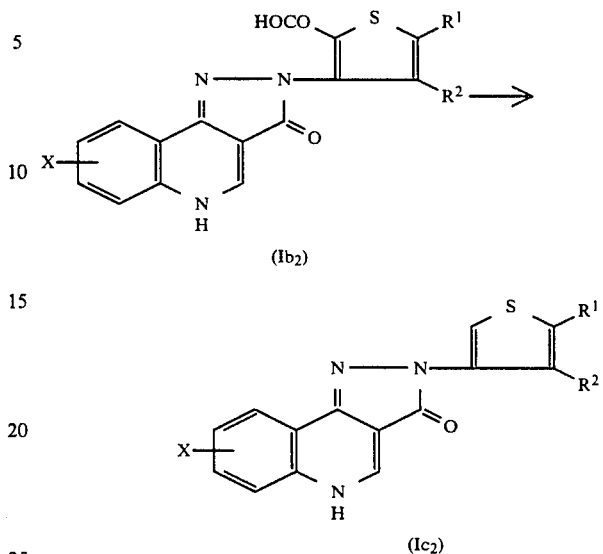

(Ib$_2$)

(Ic$_2$)

To a suspension of the compound (Ib$_2$) in quinoline is added copper powder. The mixture is stirred under nitrogen gas with heating for a period of about several 10 minutes to about several hours. After cooling, copper powder is removed by filtration. The filtrate is mixed with 1N sodium hydroxide and extracted with ether. The separated aqueous layer is filtered, and the filtrate is mixed with acetic acid. The precipitating crystals are collected by filtration, washed with water, and recrystallized from an appropriate solvent to give the compound (Ic$_2$) as yellow crystals.

The reaction conditions to prepare the compound (Ic$_2$) from the corresponding compound (Ib$_2$), yield, structural formulae, recrystallization solvent, and decomposition point of the compound (Ic$_2$) are shown in Table 6.

TABLE 6

| Ex. No. | Amount of Compound (Ib$_2$) (g) | quinoline (ml) | copper powder (g) | reaction temperature (°C.) | reaction time (min) | yield (g) | yield (%) | Compd. No. | R$^1$ | R$^2$ | X | crystal water | recrystallization solvent | dec. point (°C.) |
|---|---|---|---|---|---|---|---|---|---|---|---|---|---|---|
| 39 | 5.00 | 50 | 1.50 | 190 | 60 | 3.60 | 85 | Ic$_2$-2 | Me | H | H | ½ H$_2$O | EtOH | 298–300 |
| 40 | 0.41 | 8 | 0.12 | 200 | 30 | 0.33 | 93 | Ic$_2$-3 | H | Me | H | ½ H$_2$O | EtOH | 313–315 |
| 41 | 0.45 | 9 | 0.135 | 195 | 40 | 0.32 | 82 | Ic$_2$-4 | Me | H | 8-Me | — | MeOH | 330–332 |
| 42 | 0.737 | 7.4 | 0.24 | 195 | 70 | 0.515 | 80 | Ic$_2$-5 | Me | H | 8-MeO | H$_2$O | EtOH | 322–324 |
| 43 | 0.43 | 8 | 0.13 | 195 | 40 | 0.303 | 81 | Ic$_2$-6 | Me | H | 8-Cl | — | EtOH—CHCl$_3$ | 349–352 |
| 44 | 0.54 | 8 | 0.16 | 200 | 40 | 0.405 | 86 | Ic$_2$-7 | Me | H | 8-F | — | MeOH | 326– |

TABLE 6-continued

![structures Ib2 and Ic2]

| Ex. No. | Amount of Compound (Ib₂) (g) | quinoline (ml) | copper powder (g) | reaction temperature (°C.) | reaction time (min) | yield (g) | yield (%) | Compd. No. | R¹ | R² | X | crystal water | recrystallization solvent | dec. point (°C.) |
|---|---|---|---|---|---|---|---|---|---|---|---|---|---|---|
| 45 | 0.392 | 5 | 0.13 | 195 | 60 | 0.23 | 68 | Ic₂-8 | Me | H | 7-Me | ¼ H₂O | EtOH | 329 311–314 |
| 46 | 0.70 | 10 | 0.24 | 195 | 60 | 0.402 | 65 | Ic₂-9 | Me | H | 7-Cl | — | — | 323–327 |
| 47 | 0.40 | 3 | 0.13 | 190 | 120 | 0.28 | 80 | Ic₂-10 | Et | H | H | ¼ H₂O | EtOH | 266–268 |
| 48 | 3.67 | 33 | 1.13 | 195 | 110 | 2.80 | 86 | Ic₂-11 | Me | H | 7-MeO | ¼ H₂O | EtOH | 317–321 |

EXAMPLE 49

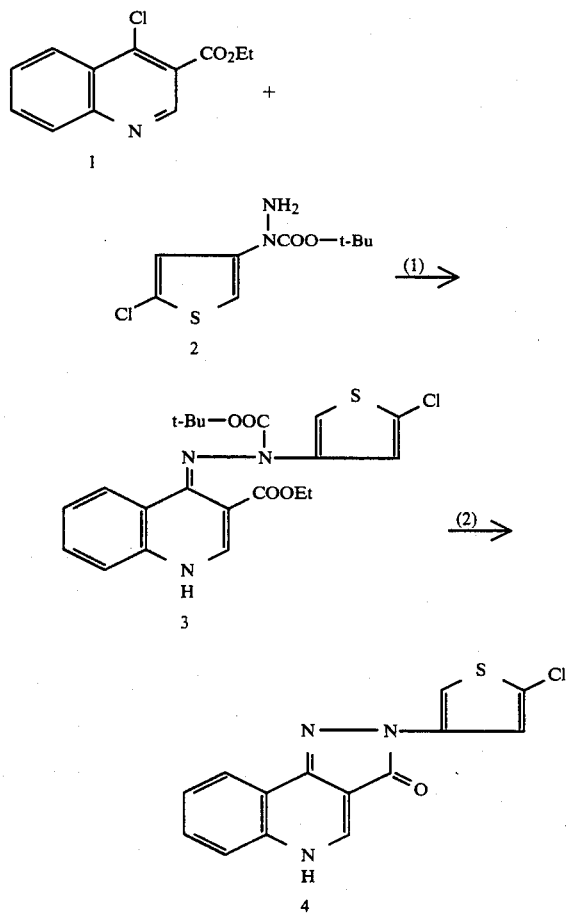

2-[3-(5-Chlorothienyl)]-2,5-dihydro-3H-pyrazolo[4,3-c]quinolin-3-one 4

(1) To a solution of 400 mg of ethyl 4-chloroquinoline-3-carboxylate 1 in 10 ml of ethanol is added 380 mg of N¹-tert-butoxycarbonyl-N¹-[3-(5-chlorothienyl)]hydrazine 2. The mixture is stirred at 40° C. for 1 hour and concentrated. The resulting residue is mixed with chloroform, washed with aqueous sodium bicarbonate and water, dried with anhydrous magnesium sulfate, and concentrated. The residue is purified by silica-gel column chromatography (benzene:ethyl acetate=30:1) to give 670 mg (yield: 93%) of ethyl 4-[N²-3-(5-chlorothienyl)-N²-t-butoxycarbonyl]hydrazinoquinoline-3-carboxylate 3.

m.p.: 134°–135° C.

(2) To a solution of 600 mg of crystalline compound 3 in 15 ml of dichloromethane is added 10 ml of trifluoroacetic acid. The mixture is stirred at 50° C. for 20 minutes and concentrated. The resulting residue is dissolved in 30 ml of ethanol and mixed with 8 ml of 1N sodium hydroxide under ice-cooling. The reaction mixture is stirred at room temperature for 1.5 hours and concentrated. The residue is mixed with 10 ml of water and extracted with ether to remove the fat-soluble portion. The aqueous layer is filtered; and the filtrate is mixed with acetic acid. The precipitating solid is collected by filtration and recrystallized from ethanol to give 210 mg of 2-[3-(5-chlorothienyl)]-2,5-dihydro-3H-pyrazolo[4,3-c]quinolin-3-one 4.

Yield: 52%.

m.p.: 287°–289° C.

NMR(DMSO-d₆): 7.45–7.82(5H, m);, 8.17–8.27(1H, m), 8.75(1H, s).

Anal. Calcd. (%) (for C₁₄H₈N₃OSCl): C, 55.73; H, 2.68; N, 13.93. Found (%): C, 55.56; H, 2.99; N, 13.56.

The reagent N¹-tert-butoxycarbonyl-N¹-[3-(5-chlorothienyl)]hydrazine 2 is prepared by subjecting 3-tert-butoxycarbonylamino-5-chlorothiophene (m.p.: 86°–87° C.) to the amination according to Synthesis, 487, 1977; and the latter is prepared from 5-chlorothiophene-3-carboxylic acid in the manner discribed as in Synthesis, 255, 1977.

EXAMPLE 50

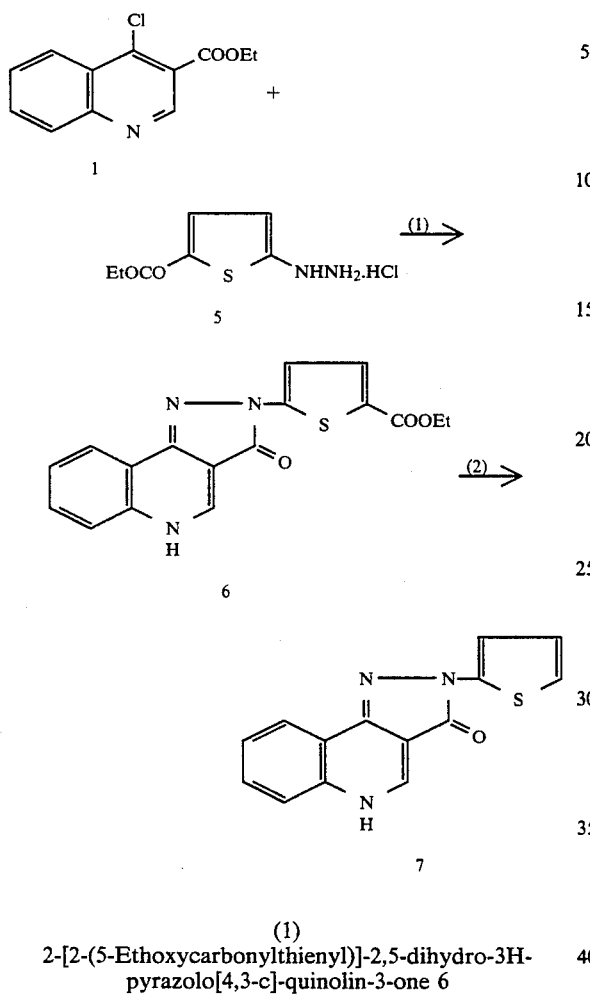

(1)
2-[2-(5-Ethoxycarbonylthienyl)]-2,5-dihydro-3H-pyrazolo[4,3-c]-quinolin-3-one 6

To a solution of 942 mg of ethyl 4-chloroquinoline-3-carboxylate 1 in 10 ml of ethanol is added 981 mg of ethyl 5-hydrazinothiophene-2-carboxylate 5 [Can. J. Chem., 44, 2881 (1966), m.p.: 160°–170° C.]. The mixture is stirred at 50°–55° C. for 30 minutes and concentrated. The resulting mixture is mixed with sodium bicarbonate, extracted with chloroform, washed with water, dried, and evaporated. The residue is purified by silica-gel column chromatography to give 645 mg (48%) of the titled compound 6 as crystals. m.p.: higher than 300° C.

NMR(DMSO-d$_6$) δ: 1.31(3H, t), 4.29(2H, q), 7.38(1H, d), 7.50–7.89 (4H, m), 8.19–8.30(1H, m), 8.88(1H, s).

(2)
2-(2-Thienyl)-2,5-dihydro-3H-pyrazolo[4,3-c]quinolin-3-one 7

To a suspension of 340 mg of the compound 6 in 5 ml of methanol is added 5 ml of 1N sodium hydroxide. The mixture is stirred at 50°–55° C. for 30 minutes. After cooling, the mixture is mixed with 4 ml of 1N hydrochloric acid, and 0.5 ml of acetic acid. The precipitating crystals are collected by filtration, washed with water, and dried. The mixture of 280 mg of 2-[2-(5-carboxy-thienyl)]-2,5-dihydro-3H-pyrazolo[4,3-c]quinolin-3-one, 3 ml of quinoline, and 140 mg of copper powder is heated at 190° C. under nitrogen gas for 20 minutes and cooled. After the removal of copper powder, the mixture is shaken with ether and 1N sodium hydroxide. The aqueous layer is separated and acetic acid is added thereto. The precipitating crystals are collected by filtration to give 210 mg (74%) of crystalline compound 7 as monohydrate.

m.p.: higher than 300° C.

NMR(DMSOd$_6$)δ:6.92–7.14(2H, m), 7.37(1H, dd), 7.50–7.75(3H, m), 8.16–8.27(1H, m), 8.77(1H, s).

EXAMPLE 51

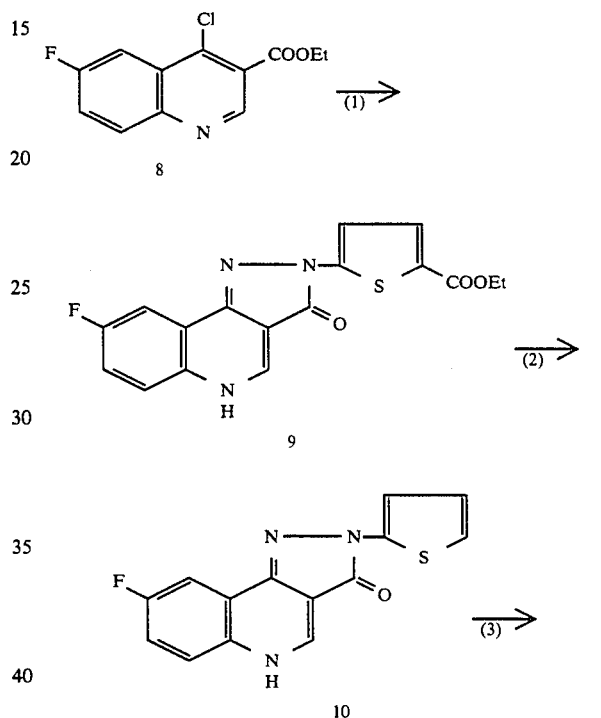

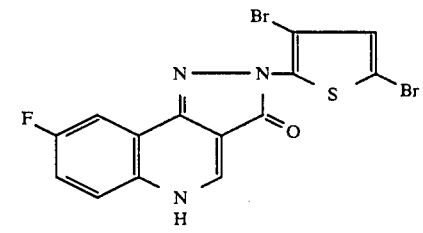

(1)
2-[2-(5-Ethoxycarbonylthienyl)]-8-fluoro-2,5-dihydro-3H-pyrazolo[4.3-c]-quinolin-3-one 9

A mixture of 1.27 g of ethyl 4-chloro-6-fluoroquinoline-3-carboxylate 8 and 1.11 g of ethyl 5-hydrazinothiophene-2-carboxylate 5 is stirred at 40° C. in 50 ml of ethanol for 1 hour. The mixture is treated in the same manner as in Example 50 to give 805 mg (45%) of the title compound 9 as crystals.

m.p.: higher than 300° 1 C.

NMR(DMSOd$_6$) δ: 1.31(3H, t), 4.28(2H, q), 7.37(1H, d), 7.48–7.96 (4H, m), 8.88(1H, s).

(2) 2-(2-Thienyl)-8-fluoro-2,5-dihydro-3H-pyrazolo[4,3-c]quinolin-3-one 10

A solution of 1.10 g of the compound 9 in 22 ml of methanol and 11 ml of 1N sodium hydroxide is heated at 60° C. for 1 hour, neutralized with hydrochloric acid, and acidified with acetic acid. The resulting crystals are collected by filtration to give a carboxylic acid. The mixture of the carboxylic acid and 270 mg of copper powder in 14 ml of quinoline is heated at 200° C. for 50 minutes. After removal of copper powder, the mixture is shaken with ether and 1N sodium hydroxide. The aqueous layer is separated and mixed with acetic acid. The precipitating crystals are collected by filtration and purified by silica-gel column chromatography to give 370 mg (48%) of the compound 10.

m.p.: higher than 300° C.

NMR(DMSOd$_6$) δ: 6.92–7.16(2H, m), 7.38(1H, dd), 7.50–7.97(3H, m), 8.82(1H, s).

(3) 2-[2-(3,5-Dibromothienyl)]-8-fluoro-2,5-dihydro-3H-pyrazolo[4,3-c]-quinoline-3-one 11

A mixture of 330 mg of the compound 10 and 495 mg of N-bromosuccinimide in carbon tetrachloride is refluxed for 3.5 hours. The reaction mixture is extracted with aqueous sodium hydroxide; and the aqueous layer is neutralized with hydrochloric acid and acidified with acetic acid. The precipitating crystals are collected by filtration and purified by silica-gel column chromatography to give 315 mg (62%) of the compound 11 as crystals.

m.p.: 277°–281° C. (d).

NMR(DMSOd$_6$) δ: 7.34(1H, s), 7.53–7.89(3H, m), 8.77(1H, s).

EXAMPLE 52

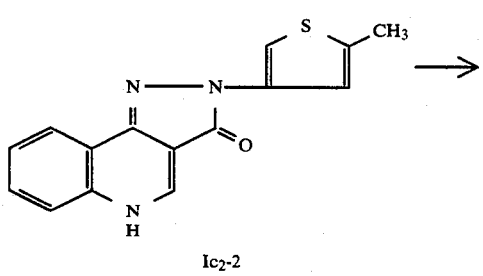

Ic$_2$-2

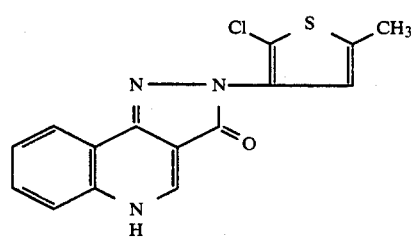

12

2-[3-(2-Chloro-5-methylthienyl)]-2,5-dihydro-3H-pyrazolo[4,3-c]-quinolin-3-one 12

To a suspension of 110 mg of 2-[3-(5-methylthienyl)]-2,5-dihydro-3H-pyrazolo[4,3-c]quinoline-3-one Ic$_2$-2 in 1 ml chloroform is added 0.42 ml of a solution of (1.3M) chlorine in carbon tetrachloride. The mixture is stirred at room temperature for 2 hours. The precipitating crystals are collected by filtration, dissolved in 1N sodium hydroxide, and mixed with acetic acid. The precipitating crystals are collected by filtration to give 77 mg (60%) of the compound 12 as crystals (¾ mole hydrate).

m.p.: 156°–160° C.

NMR(DMSOd$_6$) δ: 2.44(3H, s), 6.99–7.03(1H, m), 7.40–8.18(4H, m), 8.70(1H, s).

EXAMPLE 53

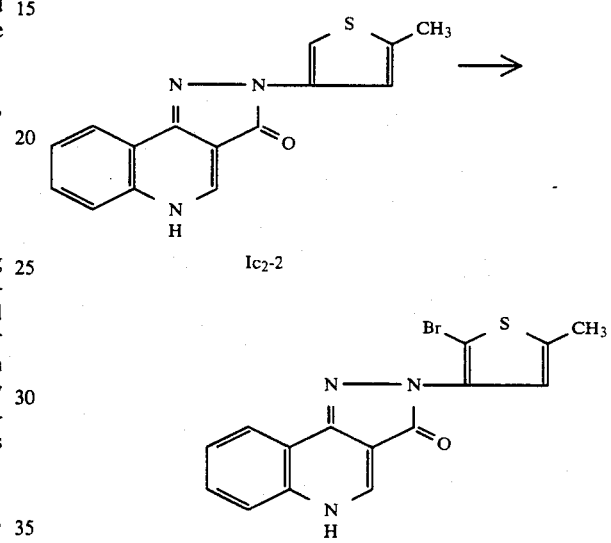

Ic$_2$-2

13

2-[3-(2-Bromo-5-methylthienyl)]-2,5-dihydro-3H-pyrazolo[4,3-c]quinoline-3-one 13

To a suspension of 196 mg of 2-[3-(5-methylthienyl)]-2,5-dihydro-3H-pyrazolo[4,3-c]quinoline-3-one Ic$_2$-2 in 5 ml of chloroform is dropwise added a solution of 160 mg of bromine in 2 ml of chloroform at room temperature, The mixture is stirred at room temperature for 2 hours. The precipitating crystals are collected by filtration to give 190 mg of the compound 13 as dihydrate.

Yield: 63%.

m.p.: 238°–243° C. (d).

NMR(DMSOd$_6$) δ: 2.44(3H, s), 6.93–6.97(1H, m), 7.40–7.75(3H, m), 8.05–8.17(1H, m), 8.68(1H, s).

EXAMPLE 54

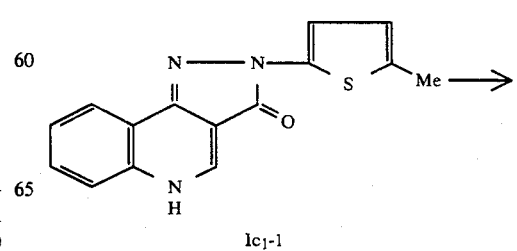

Ic$_1$-1

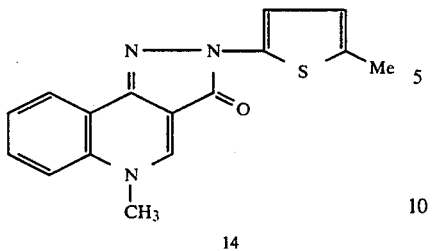

14

5-Methyl-2-[2-(5-methylthienyl)]-2,5-dihydro-3H-pyrazolo[4,3-c]quinolin-3-one 14

To a suspension of 400 mg of 2-[2-(5-methylthienyl)]-2,5-dihydro-3H-pyrazolo[4,3-c]quinolin-3-one $Ic_1$-1 in 10 ml of anhydrous tetrahydrofuran is added 60 mg of 60% sodium hydride (in mineral oil) under nitrogen gas. The mixture is refluxed for 1.5 hours and mixed with a solution of 283 mg of methyl iodide in 0.5 ml of anhydrous tetrahydrofuran with ice-cooling under stirring. The mixture is stirred at room temperature for 3 hours.

The precipitating crystals are collected by filtration and washed with a mixture of ethanol and ether. The resulting crystals are recrystallized from chloroform-methanol to give 355 mg of the compound 14 as crystals.

m.p.: 271°–274° C. (d).

Anal. Calcd. (%) (for $C_{16}H_{13}N_3OS \cdot \frac{1}{8}H_2O$): C, 64.57; H, 4.49; N, 14.12. Found (%): C, 64.45; H, 4.65; N, 14.14.

NMR(in DMSO-$d_6$) δ: 2.40(3H, d), 4.02(3H, s), 6.63 (1H, dd), 7.11(1H, d), 7.50–8.32(4H, m), 8.87(1H, s)ppm.

EXAMPLE 55

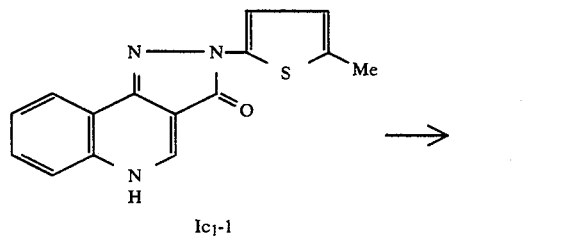

5-Acetyl-2-[2-(5-methylthienyl)]-2,5-dihydro-3H-pyrazolo[4,3-c]quinolin-3-one 15

To a suspension of 562 mg of 2-[2-(5-methylthienyl)]-2,5-dihydro-3H-pyrazolo[4,3-c]quinolin-3-one $Ic_1$-1 in 10 ml of anhydrous tetrahydrofuran is added 60 mg of 60% sodium hydride (in mineral oil) under nitrogen gas. The mixture is refluxed for 2 hours and mixed with a solution of 196 mg of acetyl chloride in 1 ml of anhydrous tetrahydrofuran under ice-cooling. The mixture is stirred at room temperature for 2 hours; and 0.1 ml of acetic acid is added thereto. The precipitating crystals are collected by filtration, washed with ether-tetrahydrofuran and water, and dried to give 520 mg of the compound 15 as crystals.

m.p.: 306°–309° C.(d).

Anal. Calcd. (%) (for $C_{17}H_{13}N_3O_2S \cdot 1/5H_2O$): C, 62.45; H, 4.14; N, 12.85. Found (%): C, 62.71; H, 4.42; N, 12.56.

NMR(DMSO$d_6$) δ: 2.43(3H, s), 2.89(3H, s), 6.67(1H, dd), 7.12(1H, dd), 7.50–8.38(4H, m), 9.00(1H, s)ppm.

EXAMPLE 56

A mixture of 281 mg of 2-[2-(5-methylthienyl)]-2,5-dihydro-3H-pyrazolo[4,3-c]quinolin-3-one $Ic_1$-1, 5 ml of trifluoroacetic acid, and 96 mg of methanesulfonic acid is stirred at room temperature for 1.5 hours and dried up under reduced pressure. The resulting residue is mixed with ethyl ether and collected by filtration to give 300 mg (yield: 80%) of the compound $Ic_1$-1 as methanesulfonate.

m.p.: 230°–234° C.(d).

Anal. Calcd. (%) (for $C_{16}H_{15}N_3O_4S_2 \cdot \frac{1}{2}H_2O$): C, 49.72; H, 4.17; N, 10.87. Found (%): C, 49.72; H, 4.16; N, 10.88.

EXAMPLE 57

A mixture of 281 mg of 2-[2-(5-methylthienyl)]-2,5-dihydro-3H-pyrazolo[4,3-c]quinoline-3-one $Ic_1$-1 in 2 ml of 0.5N sodium hydroxide is stirred for 24 hours. The reaction mixture is filtered, and the filtrate is dried up under reduced pressure. The resulting residue is washed with ether-ethanol and dried to give 185 mg (yield: 31%) of sodium salt of the compound $Ic_1$-1.

m.p.: 273°–277° C.(d).

Anal. Calcd. (%) (for $C_{15}H_{10}N_3OSNa$): C, 59.40; H, 3.32; N, 13.85. Found (%): C, 59.68; H, 3.70; N, 13.87.

EXAMPLE 58

2-{2-[5-chloro-3,4-bis(ethoxycarbonyl)thienyl]}-2,5-dihydro-3H-pyrazolo[4,3-c]quinolin-3-one $Ia_1$-13'

To a suspension of 617 mg of 2-{-2-[3,4-bis(ethoxycarbonyl)thienyl]}-2,5-dihydro-3H-pyrazolo[4,3-c]quinoline-3-one $Ia_1$-13 in 20 ml of chloroform is dropwise added 1.4 ml of a solution of 1.35M chlorine in carbon tetrachloride at 0°–5° C. The mixture is stirred at 10°–15° C. for 40 minutes and filtered; and the filtrate is concentrated. The residue is dissolved in ether and shaken with aqueous sodium hydroxide. The separated aqueous layer is neutralized with acetic acid and the precipitating crystals are collected by filtration to give 289 mg (43%) of the compound $Ia_1$-13' as yellow crystals. $Ia_1$-13' was utilized to prepare $Ib_1$-13 in Example 13.

m.p.: 152°–155° C. (d).

EXAMPLE 59

2-[3-(5-Methyl-2-methoxycarbonylthienyl)]-2,5-dihydro-3H-imidazo[4,3-c]cinnolin-3-one A

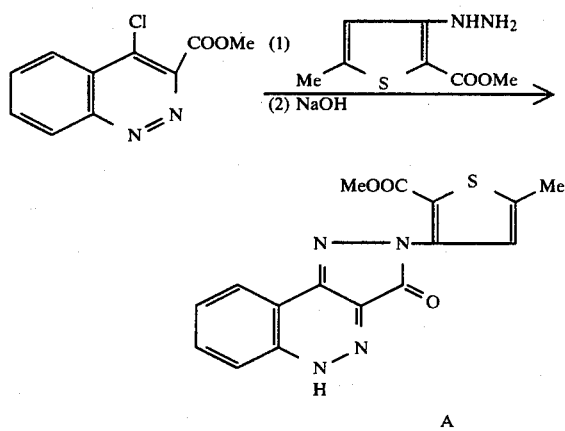

A

A solution of 500 mg of methyl 4-chlorocinnoline-3-carboxylate and 460 mg of methyl 5-methyl-3-hydrazinothiophene-2-carboxylate in 7 ml of ethanol is stirred at room temperature for 30 minutes. The mixture is concentrated and mixed with aqueous ammonia, and precipitating crystals are filtered and dried. This is stirred in a mixture of methanol (6 ml)-1N sodium hydroxide (1.2 ml) at room temperature for 1 hour and acidified with acetic acid. The resulting crystals are filtered, washed with water, and dried to give 640 mg (86%) of the compound A as crystals. This is recrystallized from ethanol to give strong red crystals.

m.p.: 295°-300° C.

EXAMPLE 60

2-[3-(5-Methylthienyl)]-2,5-dihydro-3H-imidazo[4,3-c]cinnolin-3-one B

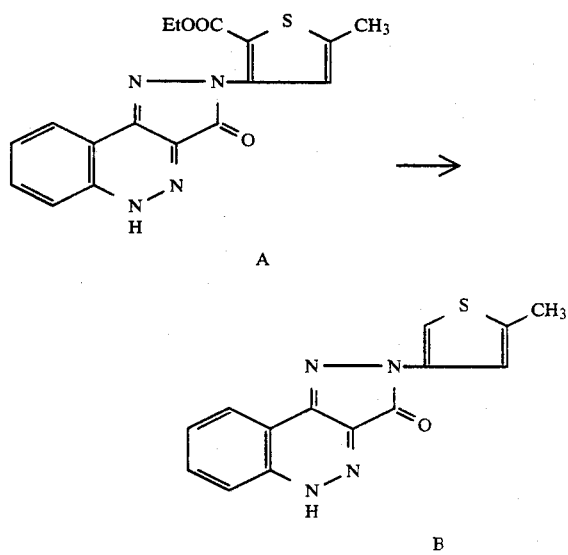

To a suspension of 330 mg of 2-[3-(5-methyl-2-methoxycarbonylthienyl))]-2,5-dihydro-3H-imidazo[4,3-c]cinnolin-3-one A in 3 ml of ethanol is added 3 ml of 1N sodium hydroxide. The mixture is refluxed for 1.5 hours, cooled and acidified with acetic acid. The precipitating crystals are filtered and dried. These crystals are suspended in 2.5 ml of quinoline and 95 mg of copper powder and heated at 195° C. for 45 minutes. After removal of copper powder, the mixture is shaken with 3 ml of 1N sodium hydroxide and ether. The separated aqueous layer is filtered by passing through celite. The filtrate is mixed with acetic acid to give 190 mg (74%) of the compound B as strong red crystals.

m.p.: >310° C.

EXAMPLE 61

2-[2-(5-Methyl-3-methoxycarbonylthienyl)]-2,5-dihydro-3H-pyrazolo[4,3-c]cinnolin-3-one C A solution of 480 mg of 4-chlorocinnoline-3-carboxylic acid and 441 mg of methyl 5-methyl-2-hydrazinothiophene-2-carboxylate in 6 ml of ethanol is stirred at room temperature for 30 minutes. The reaction mixture is concentrated and mixed with aqueous ammonia; and the precipitating crystals are filtered and dried. This is added to the mixture of 10 ml of methanol and 1.9 ml of 1N sodium hydroxide. The mixture is stirred at room temperature for 1 hour and acidified with acetic acid. The resulting crystals are filtered, washed with water, and dried to give 540 mg (73%) of the compound C as strong red crystals.

m.p.: 138°-140° C.

EXAMPLE 62

2-[2-(5-Methylthienyl)]-2,5-dihydro-3H-pyrazolo[4,3-c]cinnolin-3-one D

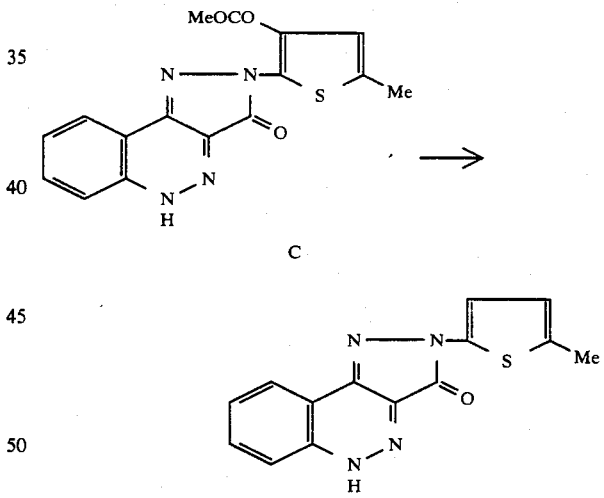

To a suspension of 420 mg of 2-[2-(5-methyl-3-methoxycarbonyl)thienyl]-2,5-dihydro-3H-pyrazolo[4,3-c]cinnolin-3-one C in 8 ml of ethanol is added 4 ml of sodium hydroxide. The mixture is refluxed for 1 hour, cooled, and acidified with acetic acid. The precipitating crystals are filtered and dried. The crystals are suspended in 3 ml of quinoline and 130 mg of copper powder. The suspension is heated at 195° C. for 1 hour. After removal of copper powder, the mixture is shaken with 4 ml of 1N sodium hydroxide. The separated aqueous layer is filtered through celite. The filtrate is mixed with acetic acid and the precipitating crystals are collected by filtration to give 200 mg (72%) of the compound D as strong red crystals.

m.p.: >310° C.

EXAMPLES 63-64

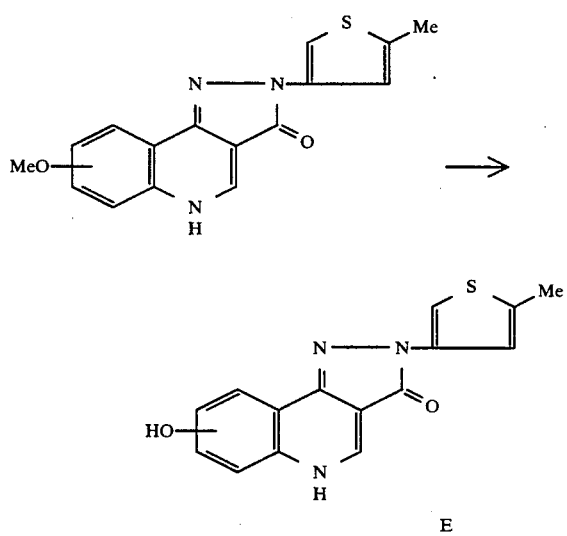

2-[3-(5-Methylthienyl)]-8-hydroxy-2,5-dihydro-3H-pyrazolo[4,3-c]quinolin-3-one E, (Example 63)

1.066 g of 2-[3-(5-methylthienyl)]-8-methoxy-2,5-dihydro-3H-pyrazolo[4,3-c]quinolin-3-one Ic$_2$-5 is dissolved in 33 ml of quinoline with heating. After cooling, the mixture is mixed with 3 ml of trimethylsilyl iodide and stirred at 190° C. for 2 hours. The reaction mixture is mixed with 40 ml of 2N hydrochloric acid, stirred for several hours, basified with 2N sodium hydroxide, and extracted with ether to remove quinoline. The aqueous layer is decolorized with active carbon and mixed with acetic acid. The precipitating crystals are collected by filtration and purified by silica-gel column chromatography. The fractions eluted by chloroform-methanol (50:3) are recrystallized from chloroform-methanol to give 797 mg (89%) of the compound $E_1$ as yellow crystals.

m.p.: >300° C.

Anal. Calcd. (%) (for $C_{15}H_{11}N_3O_2S \cdot CH_3OH$): C,58.34; H,4.59; N,12.75; S,9.73. Found (%): C,58.14; H,4.42; N,12.84; S,9.19.

2-[3-(5-Methylthienyl)]-7-hydroxy-2,5-dihydro-3H-pyrazolo[4,3-c]quinolin-3-one $E_2$ (Example 64)

A mixture of 783 mg of 2-[3-(5-methylthienyl)]-7-methoxy-2,5-dihydro-3H-pyrazolo[4,3-c]quinolin-3-one Ic$_2$-11, 25 ml of quinoline, and 2.5 ml of trimethylsilyl iodide is treated in the same manner as in Example 63 to give 389 mg (52%) of the compound $E_2$ as yellow crystals.

m.p.: 312°-318° C.

Anal. Calcd. (%) (for $C_{15}H_{11}N_3O_2S \cdot 4/5H_2O$): C,57.79; H,4.07; N,13,48; S,10.29. Found (%): C,57.75; H, 4.28; N, 13.41; S, 9.95.

EXAMPLES 65-67

5-Alkyl-2-[3-(5-methylthienyl)]-2,5-dihydro-3H-pyrazolo[4,3-c]quinolin-3-one F

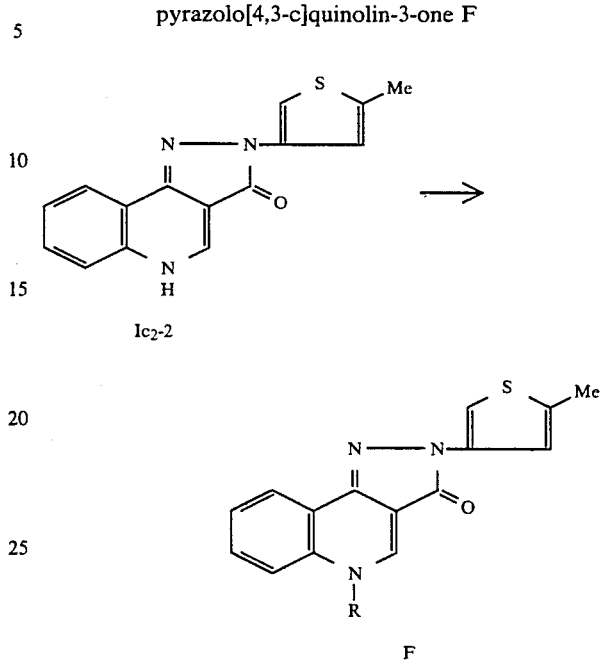

To a suspension of 1562 mg of 2-[3-(5-methylthienyl)]-2,5-dihydro-3H-pyrazolo[4,3-c]quinolin-3-one Ic$_2$-2 in 5 ml of anhydrous tetrahydrofuran is added 88 mg of 60% sodium hydride (in mineral oil). The mixture is refluxed for 2 hours and cooled. The mixture is mixed with alkyl iodide, stirred over night, and mixed with water. The precipitating crystals are filtered, washed with water, and with ethanol, and dried to give the compound F as yellow crystals.

Compounds provided are shown in the following Table.

| R | amount of RI (mg) | yield (mg) | yield (%) | m.p. (°C.) |
|---|---|---|---|---|
| Me | 300 | 452 | 76 | 253-258 (d) |
| Et | 600 | 390 | 65 | 216-218 (d) |
| n-Bu | 736 | 421 | 62 | 233-235 (d) |

EXAMPLE 68

5-Methanesulfonyl-2-[3-(5-methylthienyl)]-2,5-dihydro-3H-pyrazolo[4,3-c]quinolin-3-one G

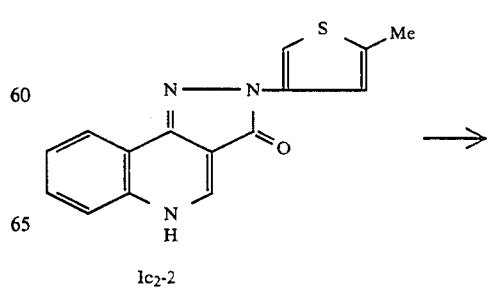

-continued

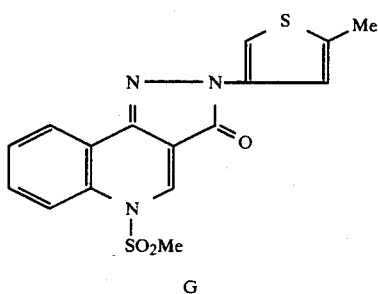

G

To a suspension of 2.86 g of 2-[3-(5-methylthienyl)]-2,5-dihydro-3H-pyrazolo[4,3-c]quinolin-3-one Ic$_2$-2 in 60 ml of anhydrous tetrahydrofuran is added 313 mg of 60% sodium hydride (mineral oil). The mixture is refluxed for 1 hour, cooled to 6° C., and to this mixture is dropwise added a solution of 1.26 g of methanesulfonyl chloride in 20 ml of anhydrous tetrahydrofuran. The mixture is stirred for 3.5 hours, concentrated under reduced pressure, mixed with water, and acicified with acetic acid. The precipitating material is collected by filtration, washed with water, dried, and recrystallized from chloroform-methanol to give 2.44 g (68%) of the orange crystalline compound G.

m.p.: 179°–182° C. (d).

Anal. Calcd. (%) (for $C_{16}H_{13}N_3O_3S_2$): C,53.46; H,3.64; N,11.69; S,17.84. Found (%): C,53.31; H,3.85; N,11.56; S,17.43.

REFERENTIAL EXAMPLE 1

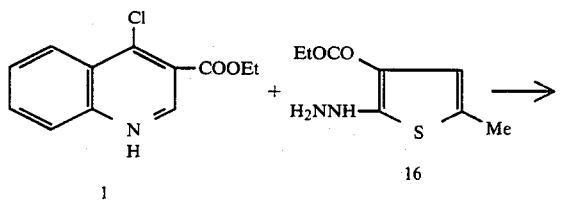

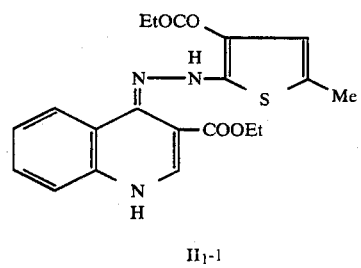

II$_1$-1

Ethyl 4-[2-(3-ethoxycarbonyl-5-methylthienyl)hydrazono]-1,4-dihydroquinoline-3-carboxylate II$_1$-1

To a solution of 942 mg of ethyl 4-chloroquinoline-3-carboxylate 1 in 10 ml of ethanol is added 880 mg of ethyl 2-hydrazino-5-methylthiophene-3-carboxylate 16. The mixture is stirred at room temperature for 1 hour and evaporated. The resulting residue is dissolved in chloroform and washed with cooled aqueous sodium bicarbonate and with water. The solution is dried over anhydrous magnesium sulfate and evaporated. The resulting solid is recrystallized from ethanol to give 1.47 g (yield: 92%) of the compound II$_1$-1 as orange crystals. m.p.: 173°–174° C.

REFERENTIAL EXAMPLES 2-13

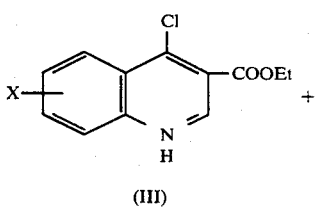

(III)

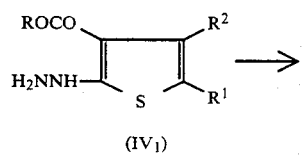

(IV$_1$)

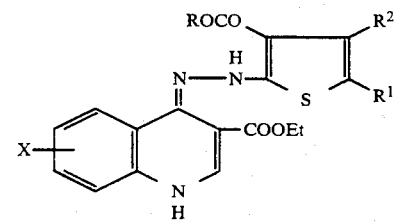

(II$_1$)

To a solution of an ethyl 4-chloroquinoline-3-carboxylate (III) in ethanol is added a 2-hydrazinothiophene-3-carboxylic acid ester (IV$_1$). The mixture is stirred at room temperature for 1 hour and evaporated. The resulting residue is dissolved in chloroform and washed with cold aqueous sodium bicarbonate and with water. The solution is dried over anhydrous magnesium sulfate and evaporated. The resulting solid is recrystallized from an appropriate solvent to give the compound (II$_1$) as orange crystals.

The reaction conditions to prepare the compound (II$_1$) from the compound (III) and the compound (IV$_1$) and physical properties of the resulting compound (II$_1$) are shown in Table 7.

TABLE 7

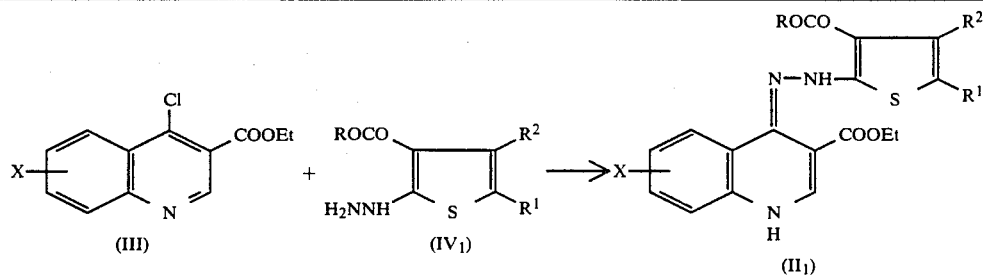

| Ref. Ex. No. | Amount (mg) Compd. (III) | Amount (mg) Compd. (IV₁) | Ethanol (ml) | Reaction temperature (°C.) | Reaction time (hrs) | Yield (g) | Yield (%) | Compd. No. | R¹ | R² | R | X | R.S. | m.p. (°C.) |
|---|---|---|---|---|---|---|---|---|---|---|---|---|---|---|
| 2 | 707 | 770 | 7 | reflux | 1 | 1.10 | 89 | II₁-2 | Et | H | Et | H | EtOH | 156-158 |
| 3 | 790 | 790 | 20 | 40 | 1 | 1.38 | 69 | II₁-3 | Me | Me | Et | H | " | 161-164 |
| 4 | 838 | 940 | 20 | " | 1 | 0.63 | 57 | II₁-4 | —(CH₂)₄— | | Et | H | " | 176-177 |
| 5 | 1500 | 1600 | 15 | reflux | 0.5 | 2.55 | 91 | II₁-5 | n-Bu | H | Me | H | " | 173-175 |
| 6 | 749 | 614 | 15 | " | 1 | 1.11 | 93 | II₁-6 | Me | H | Me | 6-Me | " | 180-182 |
| 7 | 930 | 720 | 14 | " | 1.5 | 1.27 | 88 | II₁-7 | Me | H | Me | 6-MeO | " | 164-165 |
| 8 | 810 | 614 | 25 | " | 1.5 | 1.09 | 87 | II₁-8 | Me | H | Me | 6-Cl | " | 196-197 |
| 9 | 750 | 653 | 20 | " | 1.5 | 1.05 | 88 | II₁-9 | Me | H | Me | 6-F | " | 184-186 |
| 10 | 600 | 500 | 10 | " | 1 | 0.80 | 83 | II₁-10 | Me | H | Me | 7-Me | EtOH—hexane | 169-170 |
| 11 | 1350 | 1030 | 23 | " | 1 | 1.83 | 88 | II₁-11 | Me | H | Me | 7-Cl | EtOH—hexane | 186-187 |
| 12 | 707 | 899 | 20 | 50 | 0.5 | 1.29 | 91 | II₁-12 | COOEt | Me | Et | H | EtOH | 221-224(d) |
| 13 | 1330 | 1530 | 30 | r.t. | 0.9 | 2.34 | 91 | II₁-13 | H | COOEt | Et | H | " | 178-181(d) |

*r.t.: room temperature
**R.S.: recrystallization solvent

REFERENTIAL EXAMPLE 14

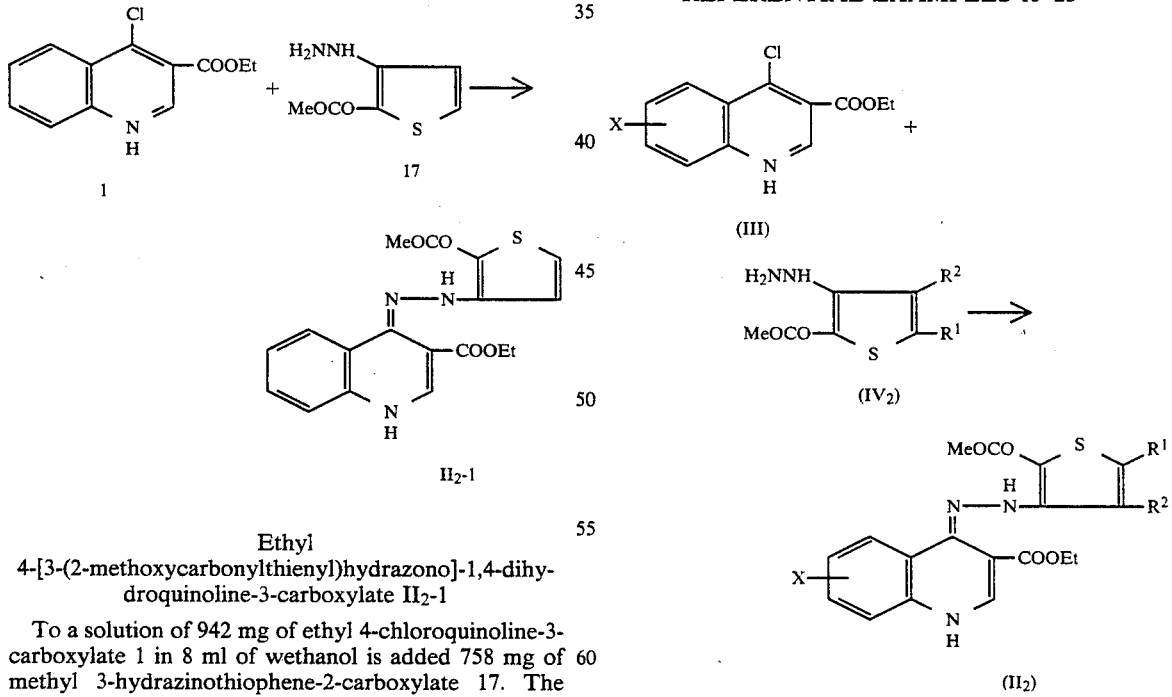

Ethyl 4-[3-(2-methoxycarbonylthienyl)hydrazono]-1,4-dihydroquinoline-3-carboxylate II₂-1

To a solution of 942 mg of ethyl 4-chloroquinoline-3-carboxylate 1 in 8 ml of wethanol is added 758 mg of methyl 3-hydrazinothiophene-2-carboxylate 17. The mixture is stirred at room temperature for 1 hour and dried up under reduced pressure. The residue is dissolved in chloroform and washed with cold aqueous sodium bicarbonate and with water. The solution is dried and evaporated to give a solid. This is recrystallized from ethanol to give 1.46 g of the compound II₂-1 as pale yellowish crystals.

m.p.: 161°-162° C.

REFERENTIAL EXAMPLES 15-23

To a solution of an ethyl 4-chloroquinoline-3-carboxylate (III) in ethanol is added a 3-hydrazinothiophene-2-carboxylic acid ester (IV₂). The mixture is stirred at room temperature for 1 hour and evaporated. The reslting residue is dissolved in chloroform and washed with cooled aqueous sodium bicarbonate and with water. The solution is dried over anhydrous magnesium sulfate and evaporated. The resulting solid is recrystallized from an appropriate solvent to give the compound ($II_2$) as crystals.

The reaction conditions to prepare the compound ($II_2$) from the compound (III) and the compound ($IV_2$), physical properties (m.p., appearance) of the resulting compound ($II_2$) are shown in Table 8.

stannous chloride in 40 ml of conc. hydrocloric acid is cooled below 5° C. in an another flask, and the solution of the diazonium salt is added thereto with stirring. The mixture is stirred at 0°-5° C. for 30 minutes; and the precipitating crystals are collected by filtration and washed with ether. The crystals are mixed with ethyl acetate, basified with 2N sodium hydroxide, and extracted with ethyl acetate. The extract is washed with

TABLE 8

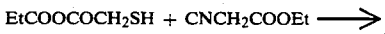

| Ref. Ex. No. | Amount (g) | | Ethanol (ml) | Reaction temperature (°C.) | Reaction time (hrs) | Compound ($II_2$) | | | | | | | |
|---|---|---|---|---|---|---|---|---|---|---|---|---|---|
| | Compd. (III) | Compd. ($IV_2$) | | | | Yield | | Compd. No. | $R^1$ | $R^2$ | X | R.S. | Appearance | m.p. (°C.) |
| | | | | | | (g) | (%) | | | | | | | |
| 15 | 8.20 | 7.12 | 80 | r.t. | 1 | 12.90 | 96 | $II_2$-2 | Me | H | H | EtOH | pale yellow | 200–201 |
| 16 | 0.471 | 0.39 | 10 | 40 | 1 | 0.738 | 96 | $II_2$-3 | H | Me | H | " | yellow | 188–191 |
| 17 | 0.749 | 0.614 | 23 | r.t. | 1 | 1.08 | 90 | $II_2$-4 | Me | H | 6-Me | " | " | 197–200 |
| 18 | 0.93 | 0.716 | 15 | " | 1 | 1.28 | 88 | $II_2$-5 | Me | H | 6-MeO | " | " | 167–168 |
| 19 | 0.450 | 0.343 | 10 | 40 | 0.7 | 0.642 | 92 | $II_2$-6 | Me | H | 6-Cl | " | pale yellow | 222–223 |
| 20 | 0.75 | 0.653 | 25 | r.t. | 1 | 1.14 | 93 | $II_2$-7 | Me | H | 6-F | " | pale yellow | 198–201 |
| 21 | 0.87 | 0.722 | 15 | " | 1 | 1.22 | 88 | $II_2$-8 | Me | H | 7-Me | " | pale yellow | 176–178 |
| 22 | 1.08 | 0.82 | 20 | " | 1 | 1.59 | 95 | $II_2$-9 | Me | H | 7-Cl | " | yellow | 198–199 |
| 23 | 0.50 | 0.445 | 5 | " | 1 | 0.71 | 84 | $II_2$-10 | Et | H | H | " | red | 166–168 |

*r.t.: room temperature
**R.S.: recrystallization solvent

REFERENTIAL EXAMPLE 24

$EtCOOCOCH_2SH + CNCH_2COOEt \longrightarrow$

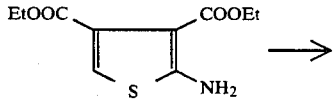

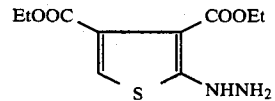

Diethyl 2-hydrazinothiophene-3,4-dicarboxylate H

To a solution of 14.3 g of ethyl mercaptopyruvate in 60 ml of ethanol is added 11.5 g of ethyl cyanoacetate at 5° C. The mixture is mixed with 0.7 ml of piperidine, stirred at room temperature for 50 minutes, and evaporated. The residue is dissolved in ethyl acetate, washed with water, and evaporated. The resulting residue is crystallized from ether-hexane to give 20.2 g (86%) of diethyl 2-aminothiophene-3,4-carboxylate as crystals, melting at 115°–118° C.

To a mixture of the crystals (4.86 g) and 30 ml of conc. hydrochloric acid is dropwise added 15 ml of an aqueous solution of 1.52 g of sodium nitrite at −10°∼5° C.; and the mixture is stirred at 15° C. for 30 minutes to give a solution of diazonium salt. A solution of 26 g of water, dried, and evaporated. The resulting residue is purified by silica-gel column chromatography and the fractions eluted with methylene chloride are concentrated to give 1.96 g (38%) of the compound H as crystals.

m.p.: 53.5°–55° C.

Preparation

2-[3-(5-Chlorothienyl)]-2,5-dihydro-3H-pyrazolo[4,3-c]quinolin-3-one: 100 mg
wheat starch: 48 mg
magnesium stearate: 2 mg The above components are mixed with each other to prepare a capsule.

Effect of the Invention

The compounds of the present invention show high affinity to a benzodiazepine receptor. The drugs bound to this receptor are classified as three groups according to the difference of the efficacy. Thus, agonists can be utilized as minor tranquilizers or anti-convulsants, antagonists can be agents for treating benzodiazepine intoxication and accidental supernumerary uptake, inverse agonists are expected as vigilance enhancing compounds.

Experiments for assessing biological activities of the compounds of the present invention are shown below; the number of the test compound corresponds to the number used in Examples and Tables respectively.

Experiment 1

Binding test to benzodiazepine receptor

This test was carried out in the modified method of Moeler & Okada, Science, 198, 849–851 (1977).

Receptor preparation was provided from the cerebral cortex of Wistar rats (male, 11 to 13 weeks age). Inhibitory action of the test compound on the specific binding of tritium labeled diazepam to the receptor was evaluated as follows. 2 nM tritium labeled diazepam and an aqueous solution of the test compound at 5 or 6 concentrations were incubated with the receptor preparation at 0° C. for 60 minutes. The 50% inhibitory concentration ($IC_{50}$) was measured by the concentration-response curve.

The inhibitory constant ($K_i$) was calculated according to the following equation, in which $K_d$ is the dissociation constant of the tritium labeled diazepam and L is the concentration of the labeled ligand.

$$Ki = \frac{IC_{50}}{1 - L/Kd}$$

The results are shown in the following table.

| Compd. No. | Ki (nM) | Compd. No. | Ki (nM) |
|---|---|---|---|
| $Ic_1$-1 | 0.35 | $Ic_2$-1 | 0.29 |
| $Ic_1$-2 | 1.51 | $Ic_2$-2 | 0.45 |
| $Ic_1$-3 | 0.63 | $Ic_2$-4 | 0.30 |
| $Ic_1$-5 | 1.53 | $Ic_2$-5 | 0.39 |
| $Ic_1$-6 | 0.22 | $Ic_2$-6 | 0.58 |
| $Ic_1$-7 | 0.17 | $Ic_2$-7 | 0.17 |
| $Ic_1$-8 | 0.31 | $Ic_2$-8 | 1.24 |
| $Ic_1$-9 | 0.14 | $Ic_2$-9 | 0.96 |
| $Ic_1$-10 | 1.44 | | |
| $Ic_1$-11 | 1.11 | | |
| $Ic_1$-12 | 0.38 | | |

Experiment 2

Inverse agonist activity was evaluated by the following procedure.

The test compound was administered orally to 8–16 male mice a group, 1 hour before a subcutaneous administration of 75 mg/kg of pentylenetetrazol (a subconvulsive dose). The dose ($ED_{50}$) at which 50% of mice died, was calculated by the Probit method.

| Compd. No. | $ED_{50}$ (mg/kg) | Note |
|---|---|---|
| $Ic_2$-2 | 1.67 | Subject matter of the invention |
| Control 1 | >200.0 | JP Unexamd. Pat. Pub. No. 56-18980 |
| Control 2 | 87.02 | JP Unexamd. Pat. Pub. No. 59-110694 |

Control 1: 2-Phenyl-2,5-dihydro-3H—pyrazolo[4,3-o]quinolin-3-one
Control 2: 2-(2-Thiazolyl)-2,5-dihydro-3H—pyrazolo[4,3-o]-quinolin-3-one

What we claim is:

1. A compound of the formula:

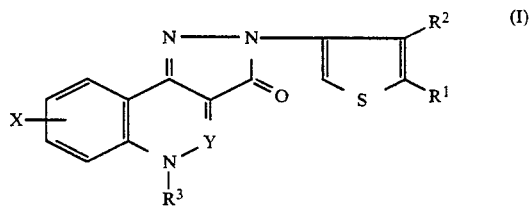

wherein $R^1$ and $R^2$ each is hydrogen, $C_1$–$C_5$ alkyl, halogen, nitro or trifluoromethyl, or $R^1$ and $R^2$ taken together may form $C_3$–$C_4$ alkylene; $R^3$ is hydrogen, $C_1$–$C_5$ alkyl, $C_1$–$C_5$ alkanoyl or $C_1$–$C_5$ alkylsulfonyl; X is hydrogen, $C_1$–$C_5$ alkyl, $C_1$–$C_5$ alkoxy, halogen or hydroxy; and Y is methine or nitrogen or a salt thereof.

2. The compound of claim 1, wherein Y is methane.
3. The compound of claim 1, wherein $R^1$ and $R^2$ each is hydrogen or $C_1$–$C_5$ alkyl.
4. The compound of claim 1, wherein X is hydrogen, $C_1$–$C_5$ alkyl, $C_1$–$C_5$ alkoxy or halogen.
5. The compound of claim 1, wherein $R^1$ and $R^2$ each is hydrogen or $C_1$–$C_5$ alkyl; $R^3$ is hydrogen; X is hydrogen or $C_1$–$C_5$ alkyl; and Y is methine.
6. The compound of claim 1, which is an organic acid addition salt of said compound of the formula (I).
7. The compound of claim 1, which is an inorganic acid addition salt of said compound of the formula (I).
8. The compound of claim 1, which is an alkali metal salt of said compound of the formula (I).
9. A pharmaceutical composition comprising:
a psychotropically effective amount of a compound of the formula:

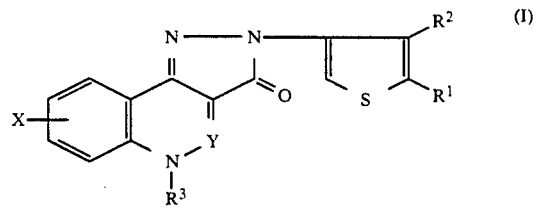

wherein $R^1$ and $R^3$ each is hydrogen, $C_1$–$C_5$ alkyl, halogen, nitro or trifluoromethyl, or $R^1$ and $R^2$ taken together may form $C_3$–$C_4$ alkylene; $R^3$ is hydrogen, $C_1$–$C_5$ alkyl, $C_1$–$C_5$ alkanoyl or $C_1$–$C_5$ alkylsulfonyl; X is hydrogen, $C_1$–$C_5$ alkyl, $C_1$–$C_5$ alkoxy, halogen or hydroxy; and Y is methine or nitrogen; or a pharmaceutically acceptable salt thereof in admixture with
a pharmaceutically acceptable diluent.

10. The composition of claim 9, in the form of a tablet.
11. The composition of claim 9, in the form of a pill.
12. A method for treating psychotropic disorders which comprises administering to a patient an effective amount of a pharmaceutical composition comprising:
a psychotropically effective amount of a compound of the formula:

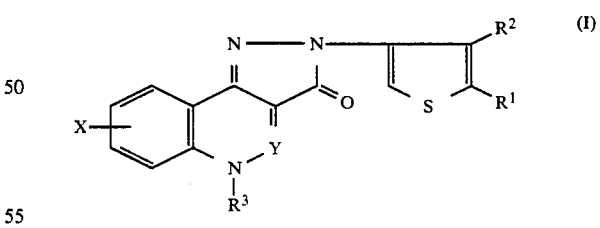

wherein $R^1$ and $R^2$ each is hydrogen, $C_1$–$C_5$ alkyl, halogen, nitro or trifluoromethyl, or $R^1$ and $R^2$ taken together may form $C_3$–$C_4$ alkylene; $R^3$ is hydrogen, $C_1$–$C_5$ alkyl, $C_1$–$C_5$ alkanoyl or $C_1$–$C_5$ alkylsulfonyl; X is hydrogen, $C_1$–$C_5$ alkyl, $C_1$–$C_5$ alkoxy, halogen or hydroxy; and Y is methine or nitrogen; or a pharmaceutically acceptable salt thereof admixture with
a pharmaceutically acceptable diluent.

13. The method of claim 12, wherein said compound of the formula (I) is administered in an amount of 0.1 to 500 mg per day.

* * * * *